US008192985B2

(12) United States Patent
Chan et al.

(10) Patent No.: US 8,192,985 B2
(45) Date of Patent: Jun. 5, 2012

(54) USE OF MOLECULAR CHAPERONES FOR THE ENHANCED PRODUCTION OF SECRETED, RECOMBINANT PROTEINS IN MAMMALIAN CELLS

(75) Inventors: Sham-Yuen Chan, El Sobrante, CA (US); Hsinyi Yvette Tang, Castro Valley, CA (US); Yiwen Tao, Albany, CA (US); Yongjian Wu, Albany, CA (US); Ruth Kelly, Richmond, CA (US)

(73) Assignee: Bayer Pharmaceuticals Corporation, Berkeley, CA (US)

( * ) Notice: Subject to any disclaimer, the term of this patent is extended or adjusted under 35 U.S.C. 154(b) by 0 days.

(21) Appl. No.: 13/115,417

(22) Filed: May 25, 2011

(65) Prior Publication Data

US 2012/0009670 A1    Jan. 12, 2012

Related U.S. Application Data

(60) Division of application No. 11/818,507, filed on Jun. 14, 2007, now Pat. No. 7,951,588, which is a continuation of application No. 10/792,571, filed on Mar. 3, 2004, now Pat. No. 7,244,616.

(60) Provisional application No. 60/483,505, filed on Jun. 27, 2003.

(51) Int. Cl.
*C12N 5/00* (2006.01)
*C12N 5/07* (2010.01)
*C12N 5/071* (2010.01)
*C12N 5/10* (2006.01)
*C12P 21/02* (2006.01)

(52) U.S. Cl. ........ 435/325; 435/352; 435/358; 435/366; 435/69.6

(58) Field of Classification Search .................. None
See application file for complete search history.

(56) References Cited

U.S. PATENT DOCUMENTS

| 4,649,132 | A | 3/1987 | Zimmerman et al. |
| 4,912,040 | A | 3/1990 | Kaufman et al. |
| 4,965,199 | A | 10/1990 | Capon et al. |
| 5,773,245 | A | 6/1998 | Wittrup et al. |
| 5,914,315 | A | 6/1999 | Sprecher et al. |
| 6,136,599 | A | 10/2000 | Cho |
| 6,333,175 | B1 | 12/2001 | Glockshuber et al. |
| 6,348,192 | B1 | 2/2002 | Chan et al. |
| 6,451,597 | B2 | 9/2002 | Dees et al. |
| 6,476,194 | B1 | 11/2002 | Tessier et al. |
| 6,583,108 | B1 | 6/2003 | Tamburini et al. |
| 7,244,616 | B2 | 7/2007 | Chan et al. |
| 2003/0194398 | A1 | 10/2003 | Tamburini et al. |

FOREIGN PATENT DOCUMENTS

| AU | 679448 | 4/1994 |
| GB | 2 237 288 | 5/1991 |
| JP | 2003501014 | 1/2003 |
| WO | WO 94/08012 | 4/1994 |
| WO | WO 97/33996 | 9/1997 |
| WO | WO 00/37099 | 6/2000 |
| WO | 00/73319 | 12/2000 |
| WO | 2005/010046 | 2/2005 |

OTHER PUBLICATIONS

Dorner et al. "Protein dissociation from GRP79 and secretion are blocked by depletion of cellular ATP levels," Proc. Natl. Acad. Sci.. USA, vol. 87, pp. 7429-7432 (Oct. 1990).
Herlitschka et al., "High expression of a B-domain deleted factor VIII gene in a human hepatic cell line," Journal of Biotechnology, vol. 61, pp. 165-173 (1998).
Michels et al., "Hsp70 and Hsp40 Chaperone Activities in the Cytoplasm and the Nucleus of Mammalian Cells," The Journal of Biological Chemistry, vol. 272, No. 52, pp. 33283-33289 (1997).
Normington et al., "*S. cerevisiae* encodes an essential protein homologous in sequence and function to mammalian BIP," Cell, vol. 57, No. 7, pp. 1223-1236 (Jun. 30, 1989) Abstract only.
Ailor, et al., "Overexpression of a Cytosolic Chaperone to Improve Solubility and Secretion of a Recombinant IgG Protein in Insect Cells", *Biotechnology and Bioengineering*, vol. 58, Nos. 2 and 3, pp. 196-203, (1998).
Ailor, et al., "Modifying secretion and post-translational processing in insect cells", *Curr. Opin. Biotechnol.*, vol. 10, pp. 142-145, (1999).
Bergeron, et al., "Calnexin: a membrane-bound chaperone of the endoplasmic reticulum", *TIBS*, vol. 19, pp. 124-128, (1994).
Chu, et al., "SV40 DNA transfection of cells in suspension: analysis of the efficiency of transcription and translation of T-antigen", *Gene*, vol. 13, pp. 197-202, (1981).
Conesa, et al., Calnexin Overexpression Increases Manganese Peroxidase Production in *Aspergillus niger*, *Applied and Environmental Microbiology*, vol. 68, No. 1, pp. 846-851, (2002).
Davis, et al., Effect of PDI Overexpression on Recombinant Protein Secretion in CHO Cells, Biotechnol. Prog., vol. 16, pp. 736-743, (2000).
Dorner, et al., "The Stress Response in Chinese Hamster Ovary Cells", *Journal of Biological Chemistry*, vol. 265, No. 35, pp. 22029-22034, (1990).
Dorner, et al., "Overexpression of GRP78 mitigates stress induction of glucose regulated proteins and blocks secretion of selective proteins in Chinese hamster ovary cells", *EMBO Journal*, vol. 11, No. 4, pp. 1563-1571, (1992).
Dunn, et. al., "Protein disulphide isomerase (PDI) is required for the secretion of a native disulphide-bonded protein from *Saccharomyces cerevisiae*", vol. 23, pp. 78S-79S, (1995).
Graham, et al., "A New Technique for the Assay of Infectivity of Human Adenovirus 5 DNA", *Virology*, vol. 52, pp. 456-467, (1973).
Hebert, et al., "Calnexin, Calreticulin, and Bip/Kar2p in Protein Folding", *Cold Spring Harbor Symposia on Quantitative Biology*, vol. LX, pp. 405-415, (1995).

(Continued)

*Primary Examiner* — Jennifer Dunston
(74) *Attorney, Agent, or Firm* — McDonnell Boehnen Hulbert & Berghoff LLP

(57) ABSTRACT

The present invention relates to a method for increased production of a secreted, recombinant protein product through the introduction of molecular chaperones in a mammalian host cell. The present invention also relates to a mammalian host cell with enhanced expression of a secreted recombinant protein product by coexpressing at least one chaperone protein.

4 Claims, 18 Drawing Sheets

OTHER PUBLICATIONS

Hsu, et al., "Effects of Co-expressing Chaperone BiP on Functional Antibody Production in the Baculovirus System", *Protein Expression and Purification*, vol. 5, pp. 595-603, (1994).

Hsu, et al., "Rescue of Immunoglobulins from Insolubility Is Facilitated by PDI in the Baculovirus Expression System", *Protein Expression and Purification*, vol. 7, pp. 281-288, (1996).

Hsu, et al., "Coexpression of Molecular Chaperone BiP Improves Immunoglobulin Solubility and IgG Secretion from *Trichoplusia ni* Insect Cells", *Biotechnol. Prog.*, vol. 13, pp. 96-104, (1997).

Ito, et al., "Calreticulin Is Directly Involved in Anti-α3 Integrin Antibody-Mediated Secretion and Activation of Matrix Metalloprotease-2", *Biochemical and Biophysical Research Communications*, vol. 283, pp. 297-302, (2001).

Kaufman, et al., "Biosynthesis, assembly and secretion of coagulation factor VIII", *Blood Coagulation and Fibrinolysis*, vol. 8, Suppl. 2, pp. S3-S14, (1997).

Kleizen, et al., "Protein folding and quality control in the endoplasmic reticulum", *Current Opinion in Cell Biology*, vol. 16, pp. 343-349, (2004).

Laskowski, et. al., "Protein Inhibitors of Proteinases", *Ann. Rev. Biochem.*, vol. 49, pp. 593-626, (1980).

Ostermeier, et al., "Eukaryotic Protein Disulfide Isomerase Complements *Escherichia coli dsbA* Mutants and Increases the Yield of a Heterologous Secreted Protein with Disulfide Bonds", J. Biol. Chem., vol. 271, No. 18, pp. 10616-10622, (1996).

Robinson, et al., Protein Disulfide Isomerase Overexpression Increases Secretion of Foreign Proteins in *Saccharomyces cerevisiae*, *Bio/Technology*, vol. 12, pp. 381-384, (1994).

Shusta, et al., "Increasing the secretory capacity of *Saccharomyces cerevisiae* for production of single-chain antibody fragments," *Nature Biotechnology*, vol. 16, pp. 773-777, (1998).

Tate, et al., "Molecular Chaperones Stimulate the Functional Expression of the Cocaine-sensitive Serotonin Transporter", *Journal of Biological Chemistry*, vol. 274, No. 25, pp. 17551-17558, (1999).

Wunderlich, et al., "In Vivo Control of Redox Potential during Protein Folding Catalyzed by Bacterial Protein Disulfide-isomerase (DsbA)", *Journal of Biological Chemistry*, vol. 268, No. 33, pp. 24547-24550, (1993).

CNX:    5' primer: ATGAATTCCGGGAGGCTAGAGATCATGG    [SEQ ID NO: 1]
        3' primer: ATTCTAGATGCAGGGGAGGAGGGAGAAG    [SEQ ID NO: 2]
CRT:    5' primer: ATGAATTCCCGCCATGCTGCTATCCGTG    [SEQ ID NO: 3]
        3' primer: ATTCTAGACTGGAGGCAGGCCTCTCTAC    [SEQ ID NO: 4]
Erp57:  5' primer: ATGAATTCCTCCGCAGTCCCAGCCGAGC    [SEQ ID NO: 5]
        3' primer: ATTCTAGACTCTCGGCCCTGAGAGGTAA    [SEQ ID NO: 6]

FIG. 1

```
                                    M  E  G  K  W  L
  1 GAATTCCGGG AGGCTAGAGA TCATGGAAGG GAAGTGGTTG
      L  C  M  L  L  V  L  G  T  A  I  V  E  A ·
 41 CTGTGTATGT TACTGGTGCT TGGAACTGCT ATTGTTGAGG
    ·  H  D  G  H  D  D  D  V  I  D  I  E  D ·
 81 CTCATGATGG ACATGATGAT GATGTGATTG ATATTGAGGA
    ·  D  L  D  D  V  I  E  E  V  E  D  S  K
121 TGACCTTGAC GATGTCATTG AAGAGGTAGA GACTCAAAA
       P  D  T  T  A  P  P  S  S  P  K  V  T  Y ·
161 CCAGATACCA CTGCTCCTCC TTCATCTCCC AAGGTTACTT
    ·  K  A  P  V  P  T  G  E  V  Y  F  A  D ·
201 ACAAAGCTCC AGTTCCAACA GGGAAGTAT ATTTGCTGA
    ·  S  F  D  R  G  T  L  S  G  W  I  L  S
241 TTCTTTTGAC AGAGGAACTC TGTCAGGGTG GATTTTATCC
       K  A  K  K  D  D  T  D  D  E  I  A  K  Y ·
281 AAAGCCAAGA AAGACGATAC CGATGATGAA ATTGCCAAAT
    ·  D  G  K  W  E  V  E  E  M  K  E  S  K ·
321 ATGATGGAAA GTGGGAGGTA GAGGAAATGA AGGAGTCAAA
    ·  L  P  G  D  K  G  L  V  L  M  S  R  A
361 GCTTCCAGGT GATAAGGAC TTGTGTTGAT GTCTCGGGCC
       K  H  H  A  I  S  A  K  L  N  K  P  F  L ·
401 AAGCATCATG CCATCTCTGC TAAACTGAAC AAGCCCTTCC
    ·  F  D  T  K  P  L  I  V  Q  Y  E  V  N ·
441 TGTTTGACAC CAAGCCTCTC ATTGTTCAGT ATGAGGTTAA
    ·  F  Q  N  G  I  E  C  G  G  A  Y  V  K
481 TTTCCAAAAT GGAATAGAAT GTGGTGGTGC CTATGTGAAA
       L  L  S  K  T  P  E  L  N  L  D  Q  F  H ·
521 CTGCTTTCTA AAACACCAGA ACTCAACCTG GATCAGTTCC
    ·  D  K  T  P  Y  T  I  M  F  G  P  D  K ·
561 ATGACAAGAC CCCTTATACG ATTATGTTTG GTCCAGATAA
    ·  C  G  E  D  Y  K  L  H  F  I  F  R  H
601 ATGTGGAGAG GACTATAAAC TGCACTTCAT CTTCCGACAC
       K  N  P  K  T  G  I  Y  E  E  K  H  A  K ·
641 AAAAACCCCA AAACGGGTAT CTATGAAGAA AAACATGCTA
    ·  R  P  D  A  D  L  K  T  Y  F  T  D  K ·
681 AGAGGCCAGA TGCAGATCTG AAGACCTATT TTACTGATAA
    ·  K  T  H  L  Y  T  L  I  L  N  P  D  N
```

FIG. 2A

```
 721 GAAAACACAT CTTTACACAC TAATCTTGAA TCCAGATAAT
       S  F  E  I  L  V  D  Q  S  V  V  N  S  G ·
 761 AGTTTTGAAA TACTGGTTGA CCAATCTGTG GTGAATAGTG
     ·  N  L  L  N  D  M  T  P  P  V  N  P  S  ·
 801 GAAATCTGCT CAATGACATG ACTCCTCCTG TAAATCCTTC
     ·  R  E  I  E  D  P  E  D  R  K  P  E  D
 841 ACGTGAAATT GAGGACCCAG AAGACCGGAA GCCCGAGGAT
        W  D  E  R  P  K  I  P  D  P  E  A  V  K ·
 881 TGGGATGAAA GACCAAAAAT CCCAGATCCA GAAGCTGTCA
     ·  P  D  D  W  D  E  D  A  P  A  K  I  P  ·
 921 AGCCAGATGA CTGGGATGAA GATGCCCCTG CTAAGATTCC
     ·  D  E  E  A  T  K  P  E  G  W  L  D  D
 961 AGATGAAGAG GCCACAAAAC CCGAAGGCTG GTTAGATGAT
        E  P  E  Y  V  P  D  P  D  A  E  K  P  E ·
1001 GAGCCTGAGT ACGTACCTGA TCCAGACGCA GAGAAACCTG
     ·  D  W  D  E  D  M  D  G  E  W  E  A  P  ·
1041 AGGATTGGGA TGAAGACATG GATGGAGAAT GGGAGGCTCC
     ·  Q  I  A  N  P  R  C  E  S  A  P  G  C
1081 TCAGATTGCC AACCCTAGAT GTGAGTCAGC TCCTGGATGT
        G  V  W  Q  R  P  V  I  D  N  P  N  Y  K ·
1121 GGTGTCTGGC AGCGACCTGT GATTGACAAC CCCAATTATA
     ·  G  K  W  K  P  P  M  I  D  N  P  S  Y  ·
1161 AAGGCAAATG GAAGCCTCCT ATGATTGACA ATCCCAGTTA
     ·  Q  G  I  W  K  P  R  K  I  P  N  P  D
1201 CCAGGGAATC TGGAAACCCA GGAAAATACC AAATCCAGAT
        F  F  E  D  L  E  P  F  R  M  T  P  F  S ·
1241 TTCTTTGAAG ATCTGGAACC TTTCAGAATG ACTCCTTTTA
     ·  A  I  G  L  E  L  W  S  M  T  S  D  I  ·
1281 GTGCTATTGG TTTGGAGCTG TGGTCCATGA CCTCTGACAT
     ·  F  F  D  N  F  I  I  C  A  D  R  R  I
1321 TTTTTTTGAC AACTTTATCA TTTGTGCTGA TCGAAGAATA
        V  D  D  W  A  N  D  G  W  G  L  K  K  A ·
1361 GTTGATGATT GGGCCAATGA TGGATGGGGC CTGAAGAAAG
     ·  A  D  G  A  A  E  P  G  V  V  G  Q  M  ·
1401 CTGCTGATGG GGCTGCTGAG CCAGGCGTTG TGGGGCAGAT
     ·  I  E  A  A  E  E  R  P  W  L  W  V  V
1441 GATCGAGGCA GCTGAAGAGC GCCCGTGGCT GTGGGTAGTC
        Y  I  L  T  V  A  L  P  V  F  L  V  I  L ·
1481 TATATTCTAA CTGTAGCCCT TCCTGTGTTC CTGGTTATCC
     ·  F  C  C  S  G  K  K  Q  T  S  G  M  E  ·
```

FIG. 2A (Continued)

```
1521 TCTTCTGCTG TTCTGGAAAG AAACAGACCA GTGGTATGGA
      · Y   K   K    T  D  A  P    Q  P  D  V    K  E
1561 GTATAAGAAA ACTGATGCAC CTCAACCGGA TGTGAAGGAA
       E   E   E    E  K  E  E    E  K  D    K  G  D  E ·
1601 GAGGAAGAAG AGAAGGAAGA GGAAAAGGAC AAGGGAGATG
      · E   E   E    G  E  E    K  L  E  E    K  Q  K ·
1641 AGGAGGAGGA AGGAGAAGAG AAACTTGAAG AGAAACAGAA
      · S  D  A    E  E  D  G    G  T  V    S  Q  E
1681 AAGTGATGCT GAAGAAGATG GTGGCACTGT CAGTCAAGAG
       E  E  D  R    K  P  K    A  E  E    D  E  I  L ·
1721 GAGGAAGACA GAAAACCTAA AGCAGAGGAG GATGAAATTT
      · N  R  S    P  R  N    R  K  P    R  R  E  * ·
1761 TGAACAGATC ACCAAGAAAC AGAAAGCCAC GAAGAGAGTG
      · *      [SEQ ID NO: 8]
1801 AAACAATCTT AAGAGCTTGA TCTGTGATTT CTTCTCCCTC
1841 CTCCCCTGCA TCTAGA    [SEQ ID NO: 7]
```

FIG. 2A (Continued)

```
                    M   L   L   S   V   P   L   L   G ·
  1 GAATTCCCGC CATGCTGCTA TCCGTGCCGC TGCTGCTCGG
    · L   L   G   L   A   V   A   E   P   A   V   Y   F
 41 CCTCCTCGGC CTGGCCGTCG CCGAGCCTGC CGTCTACTTC
      K   E   Q   F   L   D   G   D   G   W   T   S   R   W ·
 81 AAGGAGCAGT TTCTGGACGG AGACGGGTGG ACTTCCGCT
    ·   I   E   S   K   H   K   S   D   F   G   K   F   V ·
121 GGATCGAATC CAAACACAAG TCAGATTTTG GCAAATTCGT
    · L   S   S   G   K   F   Y   G   D   E   E   K   D
161 TCTCAGTTCC GGCAAGTTCT ACGGTGACGA GGAGAAAGAT
      K   G   L   Q   T   S   Q   D   A   R   F   Y   A   L ·
201 AAAGGTTTGC AGACAAGCCA GGATGCACGC TTTTATGCTC
    ·   S   A   S   F   E   P   F   S   N   K   G   Q   T ·
241 TGTCGGCCAG TTTCGAGCCT TTCAGCAACA AAGGCCAGAC
    · L   V   V   Q   F   T   V   K   H   E   Q   N   I
281 GCTGGTGGTG CAGTTCACGG TGAAACATGA GCAGAACATC
      D   C   G   G   G   Y   V   K   L   F   P   N   S   L ·
321 GACTGTGGGG GCGGCTATGT GAAGCTGTTT CCTAATAGTT
    ·   D   Q   T   D   M   H   G   D   S   E   Y   N   I ·
361 TGGACCAGAC AGACATGCAC GGAGACTCAG AATACAACAT
    · M   F   G   P   D   I   C   G   P   G   T   K   K
401 CATGTTTGGT CCCGACATCT GTGGCCCTGG CACCAAGAAG
      V   H   V   I   F   N   Y   K   G   K   N   V   L   I ·
441 GTTCATGTCA TCTTCAACTA CAAGGGCAAG AACGTGCTGA
    ·   N   K   D   I   R   C   K   D   D   E   F   T   H ·
481 TCAACAAGGA CATCCGTTGC AAGGATGATG AGTTTACACA
    · L   Y   T   L   I   V   R   P   D   N   T   Y   E
521 CCTGTACACA CTGATTGTGC GGCCAGACAA CACCTATGAG
      V   K   I   D   N   S   Q   V   E   S   G   S   L   E ·
561 GTGAAGATTG ACAACAGCCA GGTGGAGTCC GGCTCCTTGG
    ·   D   D   W   D   F   L   P   P   K   K   I   K   D ·
601 AAGACGATTG GGACTTCCTG CCACCCAAGA AGATAAAGGA
    · P   D   A   S   K   P   E   D   W   D   E   R   A
641 TCCTGATGCT TCAAAACCGG AAGACTGGGA TGAGCGGGCC
      K   I   D   D   P   T   D   S   K   P   E   D   W ·
681 AAGATCGATG ATCCCACAGA CTCCAAGCCT GAGGACTGGG
    · K   P   E   H   I   P   D   P   D   A   K   K   P
721 ACAAGCCCGA GCATATCCCT GACCCTGATG CTAAGAAGCC
    · E   D   W   D   E   E   M   D   G   E   W   E   P
```

FIG. 2B

```
 761 CGAGGACTGG GATGAAGAGA TGGACGGAGA GTGGGAACCC
       P  V  I  Q  N  P  E  Y  K  G  E  W  K  P  ·
 801 CCAGTGATTC AGAACCCTGA GTACAAGGGT GAGTGGAAGC
     ·  R  Q  I  D  N  P  D  Y  K  G  T  W  I  ·
 841 CCCGGCAGAT CGACAACCCA GATTACAAGG GCACTTGGAT
     ·  H  P  E  I  D  N  P  E  Y  S  P  D  P
 881 CCACCCAGAA ATTGACAACC CGAGTATTC  TCCCGATCCC
        S  I  Y  A  Y  D  N  F  G  V  L  G  L  D ·
 921 AGTATCTATG CCTATGATAA CTTTGGCGTG CTGGGCCTGG
     ·  L  W  Q  V  K  S  G  T  I  F  D  N  F  ·
 961 ACCTCTGGCA GGTCAAGTCT GGCACCATCT TTGACAACTT
     ·  L  I  T  N  D  E  A  Y  A  E  E  F  G
1001 CCTCATCACC AACGATGAGG CATACGCTGA GGAGTTTGGC
        N  E  T  W  G  V  T  K  A  A  E  K  Q  M ·
1041 AACGAGACGT GGGGCGTAAC AAAGGCAGCA GAGAAACAAA
     ·  K  D  K  Q  D  E  E  Q  R  L  K  E  E  ·
1081 TGAAGGACAA ACAGGACGAG GAGCAGAGGC TTAAGGAGGA
     ·  E  D  K  K  R  K  E  E  E  A  E
1121 GGAAGAAGAC AAGAAACGCA AAGAGGAGGA GGAGGCAGAG
        D  K  E  D  D  E  D  K  D  E  D  E  E  D ·
1161 GACAAGGAGG ATGATGAGGA CAAAGATGAG GATGAGGAGG
     ·  E  E  D  K  E  E  D  E  E  E  D  V  P  ·
1201 ATGAGGAGGA CAAGGAGGAA GATGAGGAGG AAGATGTCCC
     ·  G  Q  A  K  D  E  L  *      [SEQ ID NO: 10]
1241 CGGCCAGGCC AAGGACGAGC TGTAGAGAGG CCTGCCTCCA
1281 G̲T̲C̲T̲A̲G̲A̲    [SEQ ID NO: 9]
```

FIG. 2B (Continued)

```
  1 GAATTCCTCC GCAGTCCCAG CCGAGCCGCG ACCCTTCCGG
                                          M  R  L  R  R  L  ·
 41 CCGTCCCCAC CCCACCTCGC CGCCATGCGC CTCCGCCGCC
     ·  A  L  F  P  G  V  A  L  L  L  A  A  A  ·
 81 TAGCGCTGTT CCCGGGTGTG GCGCTGCTTC TTGCCGCGGC
     ·  R  L  A  A  A  S  D  V  L  E  L  T  D
121 CCGCCTCGCC GCTGCCTCCG ACGTGCTAGA ACTCACGGAC
        D  N  F  E  S  R  I  S  D  T  G  S  A  G  ·
161 GACAACTTCG AGAGTCGCAT CTCCGACACG GGCTCTGCGG
     ·  L  M  L  V  E  F  F  A  P  W  C  G  H  ·
201 GCCTCATGCT CGTCGAGTTC TTCGCTCCCT GGTGTGGACA
     ·  C  K  R  L  A  P  E  Y  E  A  A  A  T
241 CTGCAAGAGA CTTGCACCTG AGTATGAAGC TGCAGCTACC
        R  L  K  G  I  V  P  L  A  K  V  D  C  T  ·
281 AGATTAAAAG GAATAGTCCC ATTAGCAAAG GTTGATTGCA
     ·  A  N  T  N  T  C  N  K  Y  G  V  S  G  ·
321 CTGCCAACAC TAACACCTGT AATAAATATG GAGTCAGTGG
     ·  Y  P  T  L  K  I  F  R  D  G  E  E  A
361 ATATCCAACC CTGAAGATAT TTAGAGATGG TGAAGAAGCA
        G  A  Y  D  G  P  R  T  A  D  G  I  V  S  ·
401 GGTGCTTATG ATGGACCTAG GACTGCTGAT GGAATTGTCA
     ·  H  L  K  K  Q  A  G  P  A  S  V  P  L  ·
441 GCCACTTGAA GAAGCAGGCA GGACCAGCTT CAGTGCCTCT
     ·  R  T  E  E  E  F  K  K  F  I  S  D  K
481 CAGGACTGAG GAAGAATTTA AGAAATTCAT TAGTGATAAA
        D  A  S  I  V  G  F  F  D  D  S  F  S  E  ·
521 GATGCCTCTA TAGTAGGTTT TTTCGATGAT TCATTCAGTG
     ·  A  H  S  E  F  L  K  A  A  S  N  L  R  ·
561 AGGCTCACTC CGAGTTCCTA AAAGCAGCCA GCAACTTGAG
     ·  D  N  Y  R  F  A  H  T  N  V  E  S  L
601 GGATAACTAC CGATTTGCAC ATACGAATGT TGAGTCTCTG
        V  N  E  Y  D  D  N  G  E  G  I  I  L  F  ·
641 GTGAACGAGT ATGATGATAA TGGAGAGGGT ATCATCTTAT
     ·  R  P  S  H  L  T  N  K  F  E  D  K  T  ·
681 TTCGTCCTTC ACATCTCACT AACAAGTTTG AGGACAAGAC
     ·  V  A  Y  T  E  Q  K  M  T  S  G  K  I
721 TGTGGCATAT ACAGAGCAAA AAATGACCAG TGGCAAAATT
        K  K  F  I  Q  E  N  I  F  G  I  C  P  H  ·
761 AAAAAGTTTA TCCAGGAAAA CATTTTTGGT ATCTGCCCTC
     ·  M  T  E  D  N  K  D  L  I  Q  G  K  D  ·
```

FIG. 2C

```
 801 ACATGACAGA AGACAATAAA GATTTGATAC AGGGCAAGGA
       · L  L  I    A  Y  Y  D   V  D  Y    E  K  N
 841 CTTACTTATT GCTTACTATG ATGTGGACTA TGAAAAGAAC
         A  K  G   S  N  Y  W   R  N  R    V  M  M  V·
 881 GCTAAAGGTT CCAACTACTG GAGAAACAGG GTAATGATGG
       · A  K  K    F  L  D   A  G  H   K  L  N  F·
 921 TGGCAAAGAA ATTCCTGGAT GCTGGGCACA AACTCAACTT
       · A  V  A   S  R  K  T   F  S  H   E  L  S
 961 TGCTGTAGCT AGCCGCAAAA CCTTTAGCCA TGAACTTTCT
          D  F  G   L  E  S  T    A  G  E   I  P  V  V·
1001 GATTTTGGCT GGAGAGCAC TGCTGGAGAG ATTCCTGTTG
       · A  I  R    T  A  K   G  E  K   F  V  M  Q·
1041 TTGCTATCAG AACTGCTAAA GGAGAGAAGT TTGTCATGCA
       · E  E  F    S  R  D   G  K  A   L  E  R  F
1081 GGAGGAGTTC TCGCGTGATG GGAAGGCTCT GGAGAGGTTC
          L  Q  D   Y  F  D  G   N  L  K   R  Y  L  K·
1121 CTGCAGGATT ACTTTGATGG CAATCTGAAG AGATACCTGA
       · S  E  P    I  P  E   S  N  D   G  P  V  K·
1161 AGTCTGAACC TATCCCAGAG AGCAATGATG GGCCTGTGAA
       · V  V  V    A  E  N   F  D  E   I  V  N  N
1201 GGTAGTGGTA GCAGAGAATT TTGATGAAAT AGTGAATAAT
          E  N  K   D  V  L  I    E  F  Y   A  P  W  C·
1241 GAAAATAAAG ATGTGCTGAT TGAATTTTAT GCCCCTTGGT
       · G  H  C    K  N  L   E  P  K   Y  K  E  L·
1281 GTGGTCATTG TAAGAACCTG GAGCCCAAGT ATAAAGAACT
       · G  E  K   L  S  K  D   P  N  I   V  I  A
1321 TGGCGAGAAG CTCAGCAAAG ACCCAAATAT CGTCATAGCC
          K  M  D   A  T  A  N   D  V  P   S  P  Y  E·
1361 AAGATGGATG CCACAGCCAA TGATGTGCCT TCTCCATATG
       · V  R  G    F  P  T   I  Y  F   S  P  A  N·
1401 AAGTCAGAGG TTTTCCTACC ATATACTTCT CTCCAGCCAA
       · K  K  L   N  P  K  K   Y  E  G   G  R  E
1441 CAAGAAGCTA AATCCAAAGA AATATGAAGG TGGCCGTGAA
          L  S  D   F  I  S  Y    L  Q  R   E  A  T  N·
1481 TTAAGTGATT TTATTAGCTA TCTACAAAGA GAAGCTACAA
       · P  P  V    I  Q  E   E  K  P   K  K  K  K·
```

FIG. 2C (Continued)

```
1521  ACCCCCTGT  AATTCAAGAA  GAAAAACCCA  AGAAGAAGAA
       · K   A   Q      E   D   L   *      [SEQ ID NO: 12]
1561  GAAGGCACAG  GAGGATCTCT  AAAGCAGTAG  CCAAACACCA
1601  CTTTGTAAAA  GGACTCTTCC  ATCAGAGATG  GGAAAACCAT
1641  TGGGGAGGAC  TAGGACCCAT  ATGGGAATTA  TTACCTCTCA
1681  GGGCCGAGAG  TCTAGA         [SEQ ID NO: 11]
```

FIG. 2C (Continued)

```
        M   A   K   A   A   A   I   G   I   D   L   G   T   T   Y   S   C ·
   1    ATGGCCAAAG CCGCGGCGAT CGGCATCGAC CTGGGCACCA CCTACTCCTG
      · V   G   V   F   Q   H   G   K   V   E   I   I   A   N   D   Q   G ·
  51    CGTGGGGGTG TTCCAACACG GCAAGGTGGA GATCATCGCC AACGACCAGG
      · N   R   T   T   P   S   Y   V   A   F   T   D   T   E   R   L
 101    GCAACCGCAC CACCCCCAGC TACGTGGCCT TCACGGACAC CGAGCGGCTC
        I   G   D   A   A   K   N   Q   V   A   L   N   P   Q   N   T   V ·
 151    ATCGGGGATG CGGCCAAGAA CCAGGTGGCG CTGAACCCGC AGAACACCGT
      · F   D   A   K   R   L   I   G   R   K   F   G   D   P   V   V   Q ·
 201    GTTTGACGCG AAGCGGCTGA TCGGCCGCAA GTTCGGCGAC CCGGTGGTGC
      · S   D   M   K   H   W   P   F   Q   V   I   N   D   G   D   K
 251    AGTCGGACAT GAAGCACTGG CCTTTCCAGG TGATCAACGA CGGAGACAAG
        P   K   V   Q   V   S   Y   K   G   E   T   K   A   F   Y   P   E ·
 301    CCCAAGGTGC AGGTGAGCTA CAAGGGGGAG ACCAAGGCAT TCTACCCCGA
      · E   I   S   S   M   V   L   T   K   M   K   E   I   A   E   A   Y ·
 351    GGAGATCTCG TCCATGGTGC TGACCAAGAT GAAGGAGATC GCCGAGGCGT
      · L   G   Y   P   V   T   N   A   V   I   T   V   P   A   Y   F
 401    ACCTGGGCTA CCCCGTGACC AACGCGGTGA TCACCGTGCC GGCCTACTTC
        N   D   S   Q   R   Q   A   T   K   D   A   G   V   I   A   G   L ·
 451    AACGACTCGC AGCGCCAGGC CACCAAGGAT GCGGGTGTGA TCGCGGGGCT
      · N   V   L   R   I   I   N   E   P   T   A   A   A   I   A   Y   G ·
 501    CAACGTGCTG CGGATCATCA ACGAGCCCAC GGCCGCCGCC ATCGCCTACG
      · L   D   R   T   G   K   G   E   R   N   V   L   I   F   D   L
 551    GCCTGGACAG AACGGGCAAG GGGGAGCGCA ACGTGCTCAT CTTTGACCTG
        G   G   T   F   D   V   S   I   L   T   I   D   D   G   I   F ·
 601    GGCGGGGGCA CCTTCGACGT GTCCATCCTG ACGATCGACG ACGGCATCTT
      · E   V   K   A   T   A   G   D   T   H   L   G   G   E   D   F   D ·
 651    CGAGGTGAAG GCCACGGCCG GGGACACCCA CCTGGGTGGG GAGGACTTTG
      · N   R   L   V   N   H   F   V   E   E   F   K   R   K   H   K
 701    ACAACAGGCT GGTGAACCAC TTCGTGGAGG AGTTCAAGAG AAAACACAAG
        K   D   I   S   Q   N   K   R   A   V   R   R   L   R   T   A   C ·
 751    AAGGACATCA GCCAGAACAA GCGAGCCGTG AGGCGGCTGC GCACCGCCTG
      · E   R   A   K   R   T   L   S   S   S   T   Q   A   S   L   E   I ·
 801    CGAGAGGGCC AAGAGGACCC TGTCGTCCAG CACCCAGGCC AGCCTGGAGA
      · D   S   L   F   E   G   I   D   F   Y   T   S   I   T   R   A
 851    TCGACTCCCT GTTTGAGGGC ATCGACTTCT ACACGTCCAT CACCAGGGCG
        R   F   E   E   L   C   S   D   L   F   R   S   T   L   E   P   V ·
 901    AGGTTCGAGG AGCTGTGCTC CGACCTGTTC CGAAGCACCC TGGAGCCCGT
      · E   K   A   L   R   D   A   K   L   D   K   A   Q   I   H   D   L ·
 951    GGAGAAGGCT CTGCGCGACG CCAAGCTGGA CAAGGCCCAG ATTCACGACC
      · V   L   V   G   G   S   T   R   I   P   K   V   Q   K   L   L
1001    TGGTCCTGGT CGGGGGCTCC ACCCGCATCC CCAAGGTGCA GAAGCTGCTG
        Q   D   F   F   N   G   R   D   L   N   K   S   I   N   P   D   E ·
1051    CAGGACTTCT TCAACGGGCG CGACCTGAAC AAGAGCATCA ACCCCGACGA
      · A   V   A   Y   G   A   A   V   Q   A   A   I   L   M   G   D   K ·
1101    GGCTGTGGCC TACGGGGCGG CGGTGCAGGC GGCCATCCTG ATGGGGGACA
      · S   E   N   V   Q   D   L   L   L   L   D   V   A   P   L   S
1151    AGTCCGAGAA CGTGCAGGAC CTGCTGCTGC TGGACGTGGC TCCCCTGTCG
```

FIG. 2D

```
           L  G  L  E     T  A  G     G  V  M     T  A  L  I     K  R  N  ·
1201   CTGGGGCTGG AGACGGCCGG AGGCGTGATG ACTGCCCTGA TCAAGCGCAA
       ·  S  T  I     P  T  K  Q     T  Q  I     F  T  T     Y  S  D  N  ·
1251   CTCCACCATC CCCACCAAGC AGACGCAGAT CTTCACCACC TACTCCGACA
       ·  Q  P  G     V  L  I     Q  V  Y  E     G  E  R     A  M  T
1301   ACCAACCCGG GGTGCTGATC CAGGTGTACG AGGGCGAGAG GGCCATGACG
          K  D  N  N     L  L  G     R  F  E     L  S  G  I     P  P  A  ·
1351   AAAGACAACA ATCTGTTGGG GCGCTTCGAG CTGAGCGGCA TCCCTCCGGC
       ·  P  R  G     V  P  Q  I     E  V  T     F  D  I     D  A  N  G  ·
1401   CCCCAGGGGC GTGCCCAGA TCGAGGTGAC CTTCGACATC GATGCCAACG
       ·  I  L  N     V  T  A     T  D  K  S     T  G  K     A  N  K
1451   GCATCCTGAA CGTCACGGCC ACGGACAAGA GCACCGGCAA GGCCAACAAG
          I  T  I  T     N  D  K     G  R  L     S  K  E  E     I  E  R  ·
1501   ATCACCATCA CCAACGACAA GGGCCGCCTG AGCAAGGAGG AGATCGAGCG
       ·  M  V  Q     E  A  E  K     Y  K  A     E  D  E     V  Q  R  E  ·
1551   CATGGTGCAG GAGGCGGAGA AGTACAAAGC GGAGGACGAG GTGCAGCGCG
       ·  R  V  S     A  K  N     A  L  E  S     Y  A  F     N  M  K
1601   AGAGGGTGTC AGCCAAGAAC GCCCTGGAGT CCTACGCCTT CAACATGAAG
          S  A  V  E     D  E  G     L  K  G     K  I  S  E     A  D  K  ·
1651   AGCGCCGTGG AGGATGAGGG GCTCAAGGGC AAGATCAGCG AGGCCGACAA
       ·  K  K  V     L  D  K  C     Q  E  V     I  S  W     L  D  A  N  ·
1701   GAAGAAGGTG CTGGACAAGT GTCAAGAGGT CATCTCGTGG CTGGACGCCA
       ·  T  L  A     E  K  D     E  F  E  H     K  R  K     E  L  E
1751   ACACCTTGGC CGAGAAGGAC GAGTTTGAGC ACAAGAGGAA GGAGCTGGAG
          Q  V  C  N     P  I  I     S  G  L     Y  Q  G  A     G  G  P  ·
1801   CAGGTGTGTA ACCCCATCAT CAGCGGACTG TACCAGGGTG CCGGTGGTCC
       ·  G  P  G     G  F  G  A     Q  G  P     K  G  G     S  G  S  G  ·
1851   CGGGCCTGGG GGCTTCGGGG CTCAGGGTCC CAAGGGAGGG TCTGGGTCAG
       ·  P  T  I     E  E  V     D  *               [SEQ ID NO: 14]
1901   GCCCCACCAT TGAGGAGGTA GATTAG           [SEQ ID NO: 13]
```

FIG. 2D (Continued)

```
      M   G   K   D   Y   Y   Q   T   L   G   L   A   R   G   A   S   D ·
  1 ATGGGTAAAG ACTACTACCA GACGTTGGGC CTGGCCCGCG GCGCGTCGGA
    · E   E   I   K   R   A   Y   R   R   Q   A   L   R   Y   H   P   D ·
 51 CGAGGAGATC AAGCGGGCCT ACCGCCGCCA GGCGCTGCGC TACCACCCGG
    · K   N   K   E   P   G   A   E   E   K   F   K   E   I   A   E
101 ACAAGAACAA GGAGCCCGGC GCCGAGGAGA AGTTCAAGGA GATCGCTGAG
        A   Y   D   V   L   S   D   P   R   K   R   E   I   F   D   R   Y ·
151 GCCTACGACG TGCTCAGCGA CCCGCGCAAG CGCGAGATCT TCGACCGCTA
    · G   E   E   G   L   K   G   S   G   P   S   G   G   S   G   G ·
201 CGGGGAGGAA GGCCTAAAGG GGAGTGGCCC CAGTGGCGGT AGCGGCGGTG
    · A   N   G   T   S   F   S   Y   T   F   H   G   D   P   H   A
251 GTGCCAATGG TACCTCTTTC AGCTACACAT TCCATGGAGA CCCTCATGCC
        M   F   A   E   F   F   G   R   N   P   F   D   T   F   F   G ·
301 ATGTTTGCTG AGTTCTTCGG TGGCAGAAAT CCCTTTGACA CCTTTTTTGG
    · Q   R   N   G   E   E   G   M   D   I   D   D   P   F   S   G   F ·
351 GCAGCGGAAC GGGGAGGAAG GCATGGACAT TGATGACCCA TTCTCTGGCT
    · P   M   G   M   G   G   F   T   N   V   N   F   G   R   S   R
401 TCCCTATGGG CATGGGTGGC TTCACCAACG TGAACTTTGG CCGCTCCCGC
        S   A   Q   E   P   A   R   K   K   Q   D   P   P   V   T   H   D ·
451 TCTGCCCAAG AGCCCGCCCG AAAGAAGCAA GATCCCCCAG TCACCCACGA
    · L   R   V   S   L   E   E   I   Y   S   G   C   T   K   K   M   K ·
501 CCTTCGAGTC TCCCTTGAAG AGATCTACAG CGGCTGTACC AAGAAGATGA
    · I   S   H   K   R   L   N   P   D   G   K   S   I   R   N   E
551 AAATCTCCCA CAAGCGGCTA AACCCCGACG GAAAGAGCAT TCGAAACGAA
        D   K   I   L   T   I   E   V   K   K   G   W   K   E   G   T   K ·
601 GACAAAATAT TGACCATCGA AGTGAAGAAG GGGTGGAAAG AAGGAACCAA
    · I   T   F   P   K   E   G   D   Q   T   S   N   N   I   P   A   D ·
651 AATCACTTTC CCCAAGGAAG GAGACCAGAC CTCCAACAAC ATTCCAGCTG
    · I   V   F   V   L   K   D   K   P   H   N   I   F   K   R   D
701 ATATCGTCTT TGTTTTAAAG GACAAGCCCC ACAATATCTT TAAGAGAGAT
```

FIG. 2E

```
         G   S   D   V    I   Y   P    A   R   I    S   L   R   E    A   L   C  ·
751   GGCTCTGATG  TCATTTATCC  TGCCAGGATC  AGCCTCCGGG  AGGCTCTGTG
      ·  G   C   T    V   N   V   P    T   L   D    G   R   T    I   P   V   V  ·
801   TGGCTGCACA  GTGAACGTCC  CCACTCTGGA  CGGCAGGACG  ATACCCGTCG
      ·  F   K   D    V   I   R    P   G   M   R    K   V   P    G   E
851   TATTCAAAGA  TGTTATCAGG  CCTGGCATGC  GGCGAAAAGT  TCCTGGAGAA
         G   L   P   L    P   K   T    P   E   K    R   G   D    L   I   I   E  ·
901   GGCTCCCCC   TCCCCAAAAC  ACCCGAGAAA  CGTGGGGACC  TCATTATTGA
      ·  F   E   V    I   F   P    E   R   I    P   Q   T   S    R   T   V   L  ·
951   GTTTGAAGTG  ATCTTCCCCG  AAAGGATTCC  CCAGACATCA  AGAACCGTAC
      ·  E   Q   V    L   P   I    *              [SEQ ID NO: 16]
1001     TTGAGCAGGT  TCTTCCAATA  TAG        [SEQ ID NO: 15]
```

FIG. 2E (Continued)

```
       M  T  T  S  A  S  S  H  L  N  K  G  I  K  Q  V  Y ·
  1  ATGACCACCT CAGCAAGTTC CCACTTAAAT AAAGGCATCA AGCAGGTGTA
     · M  S  L  P  Q  G  E  K  V  Q  A  M  Y  I  W  I  D ·
 51  CATGTCCCTG CCTCAGGGTG AGAAAGTCCA GGCCATGTAT ATCTGGATCG
     · G  T  G  E  G  L  R  C  K  T  R  L  D  S  E
101  ATGGTACTGG AGAAGGACTG CGCTGCAAGA CCCGGACCCT GGACAGTGAG
        P  K  C  V  E  E  L  P  E  W  N  F  D  G  S  S  T ·
151  CCCAAGTGTG TGGAAGAGTT GCCTGAGTGG AATTTCGATG GCTCCAGTAC
     · L  Q  S  E  G  S  N  S  D  M  Y  L  V  P  A  A  M ·
201  TTTACAGTCT GAGGGTTCCA ACAGTGACAT GTATCTCGTG CCTGCTGCCA
     · F  R  D  P  F  R  K  D  P  N  K  L  V  L  C  E
251  TGTTTCGGGA CCCCTTCCGT AAGGACCCTA ACAAGCTGGT GTTATGTGAA
        V  F  K  Y  N  R  R  P  A  E  T  N  L  R  H  T  C ·
301  GTTTTCAAGT ACAATCGAAG GCCTGCAGAG ACCAATTTGA GGCACACCTG
     · K  R  I  M  D  M  V  S  N  Q  H  P  W  F  G  M  E ·
351  TAAACGGATA ATGGACATGG TGAGCAACCA GCACCCCTGG TTTGGCATGG
     · Q  E  Y  T  L  M  G  T  D  G  H  P  F  G  W  P
401  AGCAGGAGTA TACCCTCATG GGGACAGATG GGCACCCCTT TGGTTGGCCT
        S  N  G  F  P  G  P  Q  G  P  Y  Y  C  G  V  G  A ·
451  TCCAACGGCT TCCCAGGGCC CCAGGGTCCA TATTACTGTG GTGTGGGAGC
     · D  R  A  Y  G  R  D  I  V  E  A  H  Y  R  A  C  L ·
501  AGACAGAGCC TATGGCAGGG ACATCGTGGA GGCCCATTAC CGGGCCTGCT
     · Y  A  G  V  K  I  A  G  T  N  A  E  V  M  P  A
551  TGTATGCTGG AGTCAAGATT GCGGGGACTA ATGCCGAGGT CATGCCTGCC
        Q  W  E  F  Q  I  G  P  C  E  G  I  S  M  G  D  H ·
601  CAGTGGGAAT TCCAGATTGG ACCTTGTGAA GGAATCAGCA TGGGAGATCA
     · L  W  V  A  R  F  I  L  H  R  V  C  E  D  F  G  V ·
651  TCTCTGGGTG GCCCGTTTCA TCTTGCATCG TGTGTGTGAA GACTTTGGAG
     · I  A  T  F  D  P  K  P  I  P  G  N  W  N  G  A
701  TGATAGCAAC CTTTGATCCT AAGCCCATTC CTGGGAACTG GAATGGTGCA
```

FIG. 2F

```
              G   C   H   T   N   F   S   T   K   A   M   R   E   E   N   G   L ·
      751   GGCTGCCATA CCAACTTCAG CACCAAGGCC ATGCGGGAGG AGAATGGTCT
              · K   Y   I   E   E   A   I   E   K   L   S   K   R   H   Q   Y   H ·
      801   GAAGTACATC GAGGAGGCCA TTGAGAAACT AAGCAAGCGG CACCAGTACC
              · I   R   A   Y   D   P   K   G   G   L   D   N   A   R   R   L
      851   ACATCCGTGC CTATGATCCC AAGGGAGGCC TGGACAATGC CCGACGTCTA
              T   G   F   H   E   T   S   N   I   N   D   F   S   A   G   V   A ·
      901   ACTGGATTCC ATGAAACCTC AACATCAAC GACTTTTCTG CTGGTGTAGC
              · N   R   S   A   S   I   R   I   P   R   T   V   G   Q   E   K   K ·
      951   CAATCGTAGC GCCAGCATAC GCATTCCCCG GACTGTTGGC CAGGAGAAGA
              · G   Y   F   E   D   R   R   P   S   A   N   C   D   P   F   S
     1001   AGGGTTACTT TGAAGATCGT CGCCCCTCTG CCAACTGCGA CCCCTTTTCG
              V   T   E   A   L   I   R   T   C   L   N   E   T   G   D   E ·
     1051   GTGACAGAAG CCCTCATCCG CACGTGTCTT CTCAATGAAA CCGGCGATGA
              · P   F   Q   Y   K   N   *              [SEQ ID NO: 18]
     1101   GCCCTTCCAG TACAAAAATT AA         [SEQ ID NO: 17]
```

FIG. 2F (Continued)

```
ADRERSIHDF  CLVSKVVGRC  RASMPRWWYN      30
VTDGSCQLFV  YGGCDGNSNN  YLTKEECLKK      60
CATVTENATG  DLATSRNAAD  SSVPSAPRRQ      90
DSEDHSSDMF  NYEEYCTANA  VTGPCRASFP     120
RWYFDVERNS  CNNFIYGGCR  GNKNSYRSEE     150
ACMLRCFRQQ  ENPPLPLGSK  [SEQ ID NO: 19] 170
```

FIG. 5

USE OF MOLECULAR CHAPERONES FOR THE ENHANCED PRODUCTION OF SECRETED, RECOMBINANT PROTEINS IN MAMMALIAN CELLS

CROSS-REFERENCE

This application is a divisional of U.S. Ser. No. 11/818,507, filed Jun. 14, 2007 (now U.S. Pat. No. 7,951,588) which is a continuation of U.S. Ser. No. 10/792,571, filed Mar. 3, 2004 (now U.S. Pat. No. 7,244,616) which claims the benefit of U.S. Provisional application No. 60/483,505, filed Jun. 27, 2003, which is incorporated by reference in its entirety.

FIELD OF THE INVENTION

The present invention relates to the general field of recombinant protein production in a mammalian host cell. Specifically, the present invention relates to enhanced production of a secreted recombinant protein product by coexpressing at least one chaperone protein in the mammalian host cell.

BACKGROUND OF THE INVENTION

In both procaryotic and eucaryotic cells, molecular chaperone proteins catalyze disulfide bond exchange and assist in the proper folding of newly synthesized proteins. This observation has led to a large number of studies and proposed uses for these quality control proteins. For example, increasing pDI (protein disulfide isomerase) activity in bacterial, yeast and insect cell expression systems can have beneficial effects on protein solubility and folding and, in some cases, can lead to an increase in the secretion of heterologous proteins (1-7). In addition, other studies have shown that the molecular chaperones immunoglobulin heavy chain binding protein (BiP, also referred to as glucose regulated protein) and human heat shock protein 70 (Hsp 70) have a beneficial effect on recombinant protein expression in insect cell systems (5, 8-12).

Molecular chaperones have not had the same level of success on recombinant protein expression and secretion in mammalian cell systems. For example, overexpression of the pDI chaperone in Chinese hamster ovary (CHO) cells not only had no effect on the secretion levels of IL-15, but also caused a decrease in secretion, and an increase in cellular retention of a tumor necrosis factor receptor-Fc fusion protein (TNFR:Fc) (13). Other studies have shown that overexpression of the BiP chaperone in mammalian cells can lead to increased cellular retention and decreased secretion of recombinant proteins (14-15 and U.S. Pat. No. 4,912,040). The regulatory mechanisms involved in protein processing within the mammalian cell are complex, and probably involve the cooperation of many of these chaperone proteins. Therefore, one cannot predict whether a particular chaperone will lead to an increase in the production of a certain recombinant protein.

Because of the contradictory teaching in the field, the effect of chaperone proteins on the production of a secreted recombinant protein product is not understood and appreciated. U.S. Pat. No. 6,451,597 (the '597 patent) describes a method for enhanced production of viral particles, and speculates on the effect of chaperones on improving yield of a recombinant protein in eukaryotic cells. However, no actual expression of a recombinant protein is disclosed. However, other studies had found that over-expression of chaperones in eukaryotic cell lines either had no effect on product yields or had reduced secretion of recombinant proteins (14, 15). See also U.S. Pat. No. 4,912,040. In light of the contradictory teaching in the field, the '597 patent does not enable one of skill in the art to use chaperones to improve the production and secretion of a recombinant protein in eukaryotic cells. The state of art does not teach one to predict what effect a particular chaperone will have in the production and secretion of a given recombinant protein in cell culture models such as those described herein. The applicants were therefore surprised to find that when the chaperones described in this study were transfected into mammalian cell lines expressing a secreted, recombinant protein, the resultant effect was an overall increase in the production of the secreted protein.

SUMMARY OF THE INVENTION

The present invention relates to mammalian cells, methods and reagents therefor, for enhanced expression of a secreted recombinant protein product in a mammalian host cell.

In one aspect of the invention, a mammalian host cell for enhanced expression of a recombinant protein product is provided, said mammalian cell having genetic material coding for expression of said recombinant protein product and transformed with at least one expression vector comprising DNA encoding a chaperone protein selected from the group consisting of calnexin, calreticulin, Erp57, Hsp40, and Hsp70.

In one embodiment of the first aspect of the invention, the recombinant protein product is secreted.

In another embodiment of the invention, the genetic material coding for expression of said recombinant protein product is integrated into host cell DNA.

In another embodiment of the invention, the mammalian host cell is further transformed with an expression vector comprising DNA encoding a glutamine synthetase protein.

In another embodiment of the invention, the recombinant protein product comprises bikunin, Factor VIII, IL2SA, or fragment thereof.

In another embodiment of the invention, the transformation occurs with an expression vector comprising DNA encoding calnexin, calreticulin, Erp57, Hsp40, and Hsp70.

In another embodiment of the invention, the transformation occurs with a first expression vector comprising DNA encoding calreticulin and a second expression vector.

In a second aspect of the invention, a method for producing a mammalian host cell for enhanced expression of a target recombinant protein or fragment thereof is provided, wherein the method comprises providing a mammalian cell having genetic material coding for expression of a target recombinant protein or fragment thereof; and transforming the mammalian cell with at least one expression vector comprising DNA encoding a chaperone protein selected from the group consisting of calnexin, calreticulin, Erp57, Hsp40, and Hsp70.

In one embodiment of the second aspect of the invention, the recombinant protein product is secreted.

In another embodiment of the invention, the genetic material coding for expression of said recombinant protein product is integrated into host cell DNA.

In another embodiment of the invention, the mammalian host cell is further transformed with an expression vector comprising DNA encoding a glutamine synthetase protein.

In another embodiment of the invention, the recombinant protein product comprises bikunin, Factor VIII, IL2SA, or fragment thereof.

In another embodiment of the invention, the transformation occurs with an expression vector comprising DNA encoding calnexin, calreticulin, Erp57, Hsp40, or Hsp70.

In another embodiment of the invention, the transformation occurs with a first expression vector comprising DNA encoding calreticulin and a second expression vector comprising DNA encoding Erp57.

In a third aspect of the invention, a method for producing a secreted recombinant protein product is provided, the method comprising the steps of: culturing a mammalian host cell, said mammalian host cell having genetic material coding for expression of said recombinant protein product and transformed with at least one expression vector comprising DNA encoding a chaperone protein selected from the group consisting of calnexin, calreticulin, Erp57, hsp40, and Hsp70; and recovering from the culture medium the recombinant protein product so produced and secreted.

In one embodiment of the third aspect of the invention, the recombinant protein product is secreted.

In another embodiment of the invention, the genetic material coding for expression of said recombinant protein product is integrated into host cell DNA.

In another embodiment of the invention, the mammalian host cell is further transformed with an expression vector comprising DNA encoding a glutamine synthetase protein.

In another embodiment of the invention, the recombinant protein product comprises bikunin, Factor VIII, IL2SA, or fragment thereof.

In another embodiment of the invention, the transformation occurs with an expression vector comprising DNA encoding calnexin, calreticulin, Erp57, Hsp40, or Hsp70.

In another embodiment of the invention, the transformation occurs with a first expression vector comprising DNA encoding calreticulin and a second expression vector comprising DNA encoding Erp57.

In a fourth aspect of the invention, a method for enhancing yield of a recombinant protein or fragment thereof in a mammalian cell is provided, the method comprising providing a first cell line having genetic material coding for expression of said recombinant protein product or fragment thereof and introducing at least one chaperone protein expression vector into said first cell line so as to form a modified cell line; and selecting from said modified cell line at least one second cell line exhibiting enhanced yield of the recombinant protein or fragment thereof.

In one embodiment of the forth aspect of the invention, the recombinant protein product is secreted.

In another embodiment of the invention, the genetic material coding for expression of said recombinant protein product is integrated into host cell DNA.

In another embodiment of the invention, the mammalian host cell is further transformed with an expression vector comprising DNA encoding a glutamine synthetase protein.

In another embodiment of the invention, the recombinant protein product comprises bikunin, Factor VIII, IL2SA, or fragment thereof.

In another embodiment of the invention, the chaperone expression vector comprises DNA encoding calnexin, calreticulin, Erp57, Hsp40, or Hsp70.

In another embodiment of the invention, said introducing occurs with a first chaperone expression vector comprising DNA encoding calreticulin and a second chaperone expression vector comprising DNA encoding Erp57.

In another embodiment of the invention, at least one second cell line is produced from said first cell line by selecting a portion of said first cell line exhibiting integration of the chaperone protein expression vector into host DNA.

In a fifth aspect of the invention, a method for enhancing yield of a recombinant protein or fragment thereof in a mammalian cell is provided, the method comprises introducing genetic material coding for a recombinant protein or fragment thereof into a cell line exhibiting enhanced chaperone protein expression.

In one embodiment of this aspect of the invention, the recombinant protein product is secreted.

In another embodiment of the invention, the genetic material coding for expression of said recombinant protein product is integrated into host cell DNA.

In another embodiment of the invention, the cell is further transformed with an expression vector comprising DNA encoding a glutamine synthetase protein.

In another embodiment of the invention, the recombinant protein product comprises bikunin, Factor VIII, IL2SA, or fragment thereof.

In another embodiment of the invention, the chaperone protein comprises calnexin, calreticulin, Erp57, Hsp40, or Hsp70.

In another embodiment of the invention, the chaperone protein comprises calreticulin and Erp57.

BRIEF DESCRIPTION OF THE DRAWINGS

The invention will be better understood from a consideration of the following detailed description and claims, taken in conjunction with the drawings, in which:

FIG. 1 depicts the sequences of RT-PCR primers used to amplify cDNA of ER chaperones from a human cDNA library. Underlined indicates a built in EcoRI (5' primer) or XbaI (3' primer) restriction site. CNX:calnexin; CRT:calreticulin;

FIG. 2A depicts the complete nucleotide and amino acid sequences of calnexin cloned by RT-PCR. The 5' EcoRI and 3' XbaI sites within the primers are underlined. The start codon and stop codon are shown in bold text;

FIG. 2B depicts the complete nucleotide and amino acid sequences of calreticulin cloned by RT-PCR. The 5' EcoRI and 3' XbaI sites are underlined. The start codon and stop codon are shown in bold text;

FIG. 2C depicts the complete nucleotide and amino acid sequences of Erp57 cloned by RT-PCR. The 5' EcoRI and 3' XbaI sites are underlined. The start codon and stop codon are shown in bold text;

FIG. 2D depicts the complete nucleotide and amino acid sequences of the coding region of the human Hsp70 gene;

FIG. 2E depicts the complete nucleotide and amino acid sequences of the coding region of the human Hsp40 gene. The start codon is shown in bold and underlined text;

FIG. 2F depicts the complete nucleotide and amino acid sequences of the coding region of the glutamine synthetase gene. The start codon is shown in bold and underlined text;

20 (control cells) are super transfected with Hsp70. The experiment procedure is the same as that described in FIG. 3; and FIG. 5 depicts the amino acid sequence of bikunin.

DETAILED DESCRIPTION OF THE INVENTION

Figure 3:
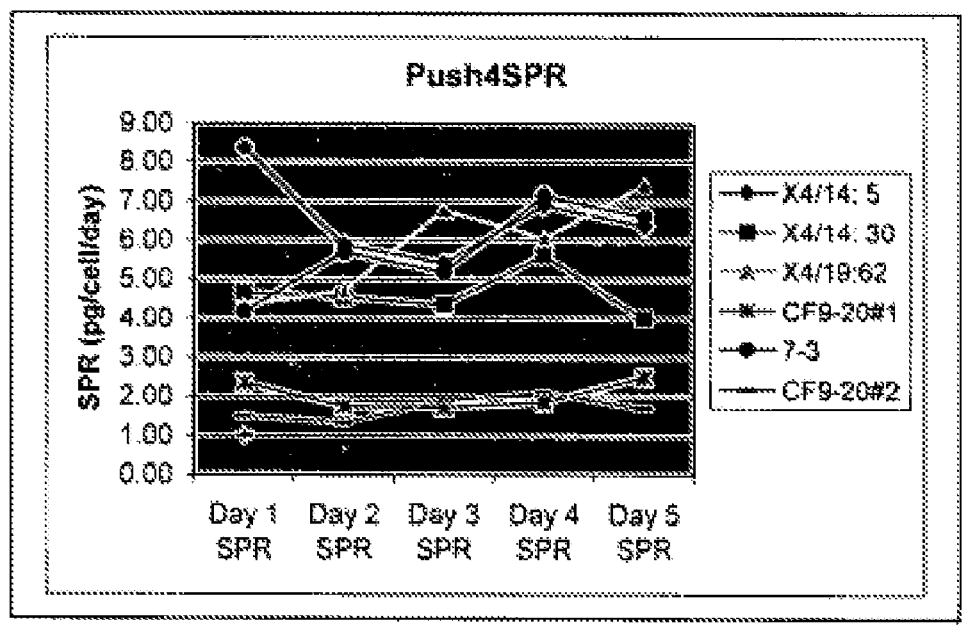
FIG. 3 is an illustration of overexpression of bikunin in clones super transfected with calnexin (X4.14:5, X4/14:30), Hsp70 (7-3) or Erp57(X4/19:62). The specific Bikunin production rate for all cell lines is expressed as pg Bikunin/cell/day (SPR). Each day cells were harvested and transferred into fresh media and incubated for 24 hours at 37° C. in shaking flasks. The following day, cells were harvested again, counted and re-suspended into fresh media of the same volume and incubated similarly for another 24 hours. Bikunin activity measurements (pg/cell/day) were conducted on samples of the spent media. The same procedure was repeated every day until the cell number and viability started to decrease. The control cell line (CF 9-20) expresses bikunin but does not express any of chaperone proteins.

The present invention relates to a method and reagents therefor, for enhanced expression of a secreted recombinant protein product in a mammalian host cell.

In one embodiment of the invention, a mammalian host cell for enhanced expression of a recombinant protein product is provided, wherein said mammalian cell comprises genetic material coding for expression of said recombinant protein product and is further transformed with at least one expression vector comprising DNA encoding a chaperone protein selected from the group consisting of calnexin, calreticulin, Erp57, Hsp40, and Hsp70.

In another embodiment of the invention, the mammalian host cell is stably transformed with the genetic material coding for expression of said recombinant protein product.

The term "mammalian host cell" is used to refer to a mammalian cell which has been transfected, or is capable of being transfected with a nucleic acid sequence and then of expressing a selected gene of interest. The term includes the progeny of the parent cell, whether or not the progeny is identical in morphology or in genetic make-up to the original parent, so long as the selected gene is present.

Suitable mammalian cells for use in the present invention include, but are not limited to Chinese hamster ovary (CHO) cells, baby hamster kidney (BHK) cells, human HeLa cells, monkey COS-1 cell, human embryonic kidney 293 cells, mouse myeloma NSO and human HKB cells (U.S. Pat. No. 6,136,599). The other cell lines are readily available from the ATCC.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

Suitable techniques of transfection for use in the present invention include, but are not limited to calcium phosphate-mediated transfection, DEAE-dextran mediated transfection, and electroporation. Cationic lipid transfection using commercially available reagents including the Boehringer Mannheim Transfection Reagent (N->1-(2,3-Dioleoyloxy)propyl-N,N,N-trimethyl ammoniummethylsulfate, Boehringer Mannheim, Indianapolis, Ind.) or LIPOFECTIN or LIPOFECTAMIN or DMRIE reagent (GIBCO-BRL, Gaithersburg, Md.) may also be used.

As used herein the term "super transfection" refers to transfecting more than one expression vectors to a host cell already expressing a recombinant gene.

The term "transformation" as used herein refers to a change in a cell's genetic characteristics, and a cell has been transformed when it has been modified to contain a new DNA. For example, a cell is transformed where it is genetically modified from its native state. Following transfection, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

As used herein the term "modified cell line" refers to a cell line either transiently or stably transformed with one or more DNA constructs.

Polynucleotides, genetic material, recombinant DNA molecules, expression vectors, and such, used in the practice of the present invention may be isolated using standard cloning methods such as those described by Sambrook et al. (Molecular Cloning: A Laboratory Manual, Second Edition, Cold Spring Harbor, N.Y., 1989; which is incorporated herein by reference). Alternatively, the polynucleotides coding for a recombinant protein product of the present invention may be synthesized using standard techniques that are well known in the art, such as by synthesis on an automated DNA synthesizer. For example, in one embodiment of the invention, DNA sequences encoding the calnexin protein are synthesized by RT-PCR using primers depicted in FIG. 1.

As used herein an "expression vector" refers to a DNA molecule, or a clone of such a molecule, which has been modified through human intervention to contain segments of DNA combined and juxtaposed in a manner that would not otherwise exist in nature. DNA constructs may be engineered to include a first DNA segment encoding a polypeptide of the present invention operably linked to additional DNA segments required for the expression of the first DNA segment. Within the context of the present invention additional DNA segments will generally include promoters and transcription terminators and may further include enhancers and other elements. One or more selectable markers may also be included. DNA constructs useful for expressing cloned DNA segments in a variety of prokaryotic and eukaryotic host cells can be prepared from readily available components or purchased from commercial suppliers.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptide from the mature protein as it passes through the secretory pathway. A recombinant protein may contain a secretory signal sequence in its original amino acid sequence, or may be engineered to become a secreted protein by inserting an engineered secretory signal sequence into its original amino acid sequence. The choice of suitable promoters, terminators and secretory signals is well within the level of ordinary skill in the art. Expression of cloned genes in cultured mammalian cells and in *E. coli*, for example, is discussed in detail in Sambrook et al. (Molecular Cloning: A Laboratory Manual, Second Edition, Cold Spring Harbor, N.Y., 1989; which is incorporated herein by reference).

As used herein, the term "recombinant protein product" refers to a recombinant protein or fragment thereof expressed from the genetic material introduced into the host mammalian cell.

After transfection, the cell may be maintained either transiently transformed or stably transformed with said DNA construct. Introduction of multiple DNA constructs, and selection of cells containing the multiple DNA constructs can be done either simultaneously or, more preferably, sequentially. The technique of establishing a cell line stably transformed with a genetic material or expression vector is well known in the art (Current Protocols in Molecular Biology). In general, after transfection, the growth medium will select for cells containing the DNA construct by, for example, drug selection or deficiency in an essential nutrient, which is complemented by a selectable marker on the DNA construct or co-transfected with the DNA construct. Cultured mammalian cells are generally cultured in commercially available serum-containing or scrum-free medium. Selection of a medium appropriate for the particular host cell used is within the level of ordinary skill in the art.

Suitable selectable markers for drug selection used in this invention include, but are not limited to, neomycin (G418), hygromycin, puromycin, zeocin, colchine, methotrexate, and methionine sulfoximine.

Once a drug resistant cell population is established, individual clones may be selected and screened for high expressing clones. Methods of establishing cloned cell line are well known in the art, including, but not limited to, using a cloning cylinder, or by limiting dilution. Expression of the recombinant product of interest from each clone can be measured by methods such as, but not limited to, immunoassay, enzymatic assay, or chromogenic assay.

Cell line stably transformed with a first DNA construct may be then used as host cell for transfection with a second or more DNA constructs, and subjected to different drug selections.

In one embodiment of the invention, a mammalian host cell with enhanced expression and secretion of bikunin protein or fragment thereof is provided, wherein the mammalian host cell is further transformed with at least one expression vector comprising DNA encoding a chaperone protein selected from the group consisting of calnexin, calreticulin, Erp57, Hsp40, and Hsp70.

In a preferred embodiment of the invention, the mammalian host cell with enhanced expression and secretion of bikunin is a CHO cell.

As used herein the term "bikunin" refers to any protein, which has at least one Kunitz domain. Kunitz-type domains have been described in references such as Laskowski et al., 1980, Ann Rev Biochem. 49:593-626; and U.S. Pat. No. 5,914,315 (Jun. 22, 1999). In one preferred embodiment, the term bikunin used herein refers to the amino acid sequence shown in FIG. 5. Other bikunin proteins and fragments thereof are described in U.S. application Ser. Nos. 09/144,428, 09/974,026, 09/218,913, and 09/441,966, and PCT Application serial numbers US97/03894, published as WO 97/33996, and US99/04381, published as WO 00/37099, which are incorporated herein by reference)

In another embodiment of the invention, the invention provides a mammalian host cell with enhanced expression and secretion of Factor VIII protein or fragment thereof, and the mammalian host cell is further transformed with at least one expression vector comprising DNA encoding a chaperone protein selected from the group consisting of calnexin, calreticulin, Erp57, Hsp40, and Hsp70.

In one preferred embodiment, the Factor VIII protein has the sequence depicted in U.S. Pat. No. 4,965,199 (incorporated herein by reference in its entirety).

In yet another preferred embodiment, the mammalian host cell with enhanced expression and secretion of Factor VIII is a BHK cell.

In another embodiment of the invention, the invention provides a mammalian host cell with enhanced expression and secretion of IL2SA protein or fragment thereof, and the mammalian host cell is further transformed with at least one expression vector comprising DNA encoding a chaperone protein selected from the group consisting of calnexin, calreticulin, Erp57, Hsp40, and Hsp70.

In one preferred embodiment, the IL2SA protein has the sequence depicted in U.S. Pat. No. 6,348,192 (incorporated herein by reference in its entirety).

In yet another preferred embodiment, the mammalian host cell with enhanced expression and secretion of IL2SA is a CHO cell.

In still another embodiment of the invention, the mammalian host cell is further transformed with an expression vector encoding a glutamine synthetase protein.

The present invention also provides a method for producing a mammalian host cell for enhanced expression of a target recombinant protein or fragment thereof comprising: providing a mammalian cell having genetic material coding for expression of a target recombinant protein or fragment thereof; and transforming the mammalian cell with at least one expression vector comprising DNA encoding a chaperone protein selected from the group consisting of calnexin, calreticulin, Erp57, Hsp40, and Hsp70.

In one embodiment of the invention, the genetic material coding for expression of said recombinant protein product is integrated into host cell DNA.

In another embodiment of the invention, the mammalian host cell is further transformed with an expression vector comprising DNA encoding a glutamine synthetase protein.

In one preferred embodiment of the invention, the recombinant protein product is bikunin or fragment thereof and the transformation occurs with an expression vector comprising DNA encoding calnexin, Erp57, calreticulin, or Hsp70.

In another preferred embodiment of the invention, the recombinant protein product is Factor VIII or fragment thereof and the transformation occurs with a first expression vector comprising DNA encoding calreticulin and a second expression vector comprising DNA encoding Erp57.

In another preferred embodiment of the invention, the recombinant protein product is Factor VIII or fragment thereof and the transformation occurs with an expression vector comprising DNA encoding calnexin or Hsp70.

In another preferred embodiment of the invention, the recombinant protein product is IL2SA or fragment thereof and the transformation occurs with an expression vector comprising DNA encoding Hsp70.

The present invention also provides a method for producing a secreted recombinant protein product comprising culturing a mammalian host cell, said mammalian host cell having a genetic material coding for expression of said recombinant product and further transformed with at least one expression vector comprising DNA encoding a chaperone protein elected from the group consisting of calnexin, calreticulin, Erp57, Hsp40, and Hsp70; and recovering from the culture medium the bikunin protein or fragment thereof so produced and secreted.

In one embodiment of the invention, the method for producing a secreted recombinant protein product comprising culturing a mammalian host cell, wherein the mammalian host cell is stably transformed with a genetic material coding for the expression of said recombinant product.

In another embodiment of the invention, the method for producing a secreted recombinant protein product further comprises transfecting the mammalian host cell with an expression vector encoding a glutamine synthetase protein.

One embodiment of the invention provides a method of producing a bikunin protein or fragment thereof, comprising culturing a mammalian host cell expressing bikunin or fragment thereof, and at least one of the chaperone proteins selected from the group consisting of calnexin, calreticulin, Erp57, Hsp40, and Hsp70; and recovering from the culture medium the bikunin protein or fragment thereof so produced and secreted.

In one embodiment of the invention, a method for enhanced production of a recombinant bikunin protein in a CHO cell is provided, wherein a genetic material coding for expression of said recombinant bikunin has been previously introduced into a first CHO cell line (as described in U.S. patent application Ser. No. 09/441,654 to Chan filed Nov. 12, 1999, incorporated herein by reference), comprising the steps of: inserting at least one chaperone protein expression vector into said first CHO cell line so as to form a modified CHO cell line; and selecting from said modified CHO cell line at least one second cell exhibiting enhanced yield of the recombinant bikunin protein.

In another embodiment of the invention, the method for enhancing recombinant bikunin yield in a CHO cell line comprises introducing a genetic material for such bikunin into a CHO cell line, wherein the CHO cell line exhibits enhanced chaperone protein expression.

In yet another embodiment of the invention, a method for enhanced production of a recombinant Factor VIII protein in a BHK cells is provided, wherein a genetic material coding for expression of said recombinant Factor VIII has been previously introduced into a first BHK cell line, comprising the steps of: inserting at least one chaperone protein expression vector into said first BHK cell line so as to form a modified BHK cell line; and selecting from said modified BHK cell line at least one second cell exhibiting enhanced yield of the recombinant Factor VIII protein.

In still another embodiment of the invention, the method for enhancing recombinant Factor VIII yield in a BHK cell line comprises introducing a genetic material for such Factor VIII into a BHK cell line, wherein the BHK cell line exhibits enhanced chaperone protein expression.

The present invention also provides a method for enhanced production of a recombinant IL2SA protein into a CHO cell, wherein a genetic material coding for expression of said recombinant IL2SA has been previously introduced into a first CHO cell line, comprising the steps of: inserting at least one chaperone protein expression vector into said first CHO cell line so as to form a modified CHO cell line; and selecting from said modified CHO cell line at least one second cell exhibiting enhanced yield of the recombinant IL2SA protein.

In another embodiment of the invention, the method for enhancing recombinant IL2SA yield in a CHO cell line comprises introducing a genetic material for such IL2SA into a CHO cell line, wherein the CHO cell line exhibits enhanced chaperone protein expression.

The following examples are intended for illustration purposes only, and should not be construed as limiting the scope of the invention in any way.

EXAMPLES

Example 1

Cloning of Chaperone cDNA

All chaperone sequences were cloned from human cDNA libraries followed by verification of the nucleotide sequences. DNA sequences representing the three ER chaperones were cloned by RT-PCR from a human cDNA library. The RT-PCR primers used in these reactions were designed to amplify the entire coding region using the appropriate sequences obtained from Genbank. Each pair of 5' and 3' primers include either an EcoRI (5' primer) or XbaI (3' primer) restriction site (FIG. 1) to facilitate cloning of the PCR product into the expression vector, pCI-neo (Promega).

The PCR reactions were performed using high fidelity PFU enzyme (Stratagene). Bands of the expected size were purified, digested with EcoR I and Xba I and cloned into the similarly digested pCI-neo vector. Recombinant vectors from this step were propagated in *E. Coli* followed by isolation and purification of the vector sequences. The sequence inserts representing the chaperones were sequenced using primers binding just outside the multiple cloning sites of the vector as well as within the chaperone sequence. Sequencing was done using the Big Dye terminator method on MJ Research's thermal cycler and analyzed using an ABI 310 Genetic Analyzer. The cDNA sequences of human calnexin, clareticulin and Erp57 are shown in FIGS. 2A-2C.

The full-length human Hsp70 cDNA fragment was obtained by RT-PCR using human brain polyA$^+$ RNA (CLONTECH Cat: 6516-1) and two primers designated F-Hsp70=5'AGG GAA CCG CAT GGC CAA AG and R-Hsp70=5' GAA AGG CCCCTA ATC TAC CTC CTC A. The primer sequences of Hsp 70 were derived from the previously published sequence for the human heat shock protein (Hsp70) gene [9]. The F-Hsp70 and R-Hsp70 primers included either an EcoRI or XbaI sequence respectively. The desired PCR fragment was purified by agarose gel electrophoresis and confirmed by nucleotide sequencing. The full-length human Hsp70 cDNA fragment was then inserted into the EcoRI and XbaI cloning sites of the pCI-neo vector to form the pCI-neo-Hsp70 vector. The pCI-neo-Hsp70 vector was propagated in *E. Coli* followed by isolation and purification of the vector sequences. pCI-neo-Hsp70 plasmid DNA was sequenced by ABI PRISM 310 Genetic Analyzer. The sequence of human Hsp70 is shown in FIG. 2D.

Example 2

Bikunin Production is Increased in CHO Cells after Transfection of an ER Chaperone Such as Calnexin, Calreticulin, Erp57 or Hsp70

A CHO cell line secreting the Bikunin recombinant protein (U.S. patent application Ser. No. 09/441,654, incorporated herein by reference) was super transfected with various combinations of the ER chaperones, calnexin (CNX), calreticulin (CRT), ERp57 or Hsp70 followed by selection with G418. Populations were obtained and screened by kallikrein assay (U.S. patent application Ser. No. 09/441,654, incorporated herein by reference). Briefly, bikunin standarts or culture fluid was serially diluted and incubated with an equal volume of kallikrein at 37° C. for 30 minutes, after which a chromogenic substrate, N-benzoyl-Pro-Phe-Arg-pNA, was added. The reaction was incubated for 15 minutes before the addition of 50% acetic acid. The amount of p-nitroanilide released was measured at 405 nM. Populations showing the highest Bikunin titers were then single cell cloned and growth expanded over a period of several weeks. Clones showing consistently higher Bikunin titers (2-4×) relative to the control CF9-20 cells were retained and expanded into shake flasks for further analysis. These clones were further narrowed based on Bikunin titers and growth characteristics demonstrated while growing in the shake flask environment. Final candidate clones were selected after several rounds and extensive analyses at the shake flask stage.

The specific Bikunin production rate for all cell lines is expressed as pg Bikunin/cell/day (SPR). Each day cells were harvested and transferred into fresh media and incubated for 24 hours at 37° C. in shaking flasks. The following day, cells were harvested again, counted and re-suspended into fresh media of the same volume and incubated similarly for another 24 hours. Bikunin activity measurements (pg/cell/day) were conducted on samples of the spent media. The same procedure was repeated every day until the cell number and viability started to decrease.

Figure 4:
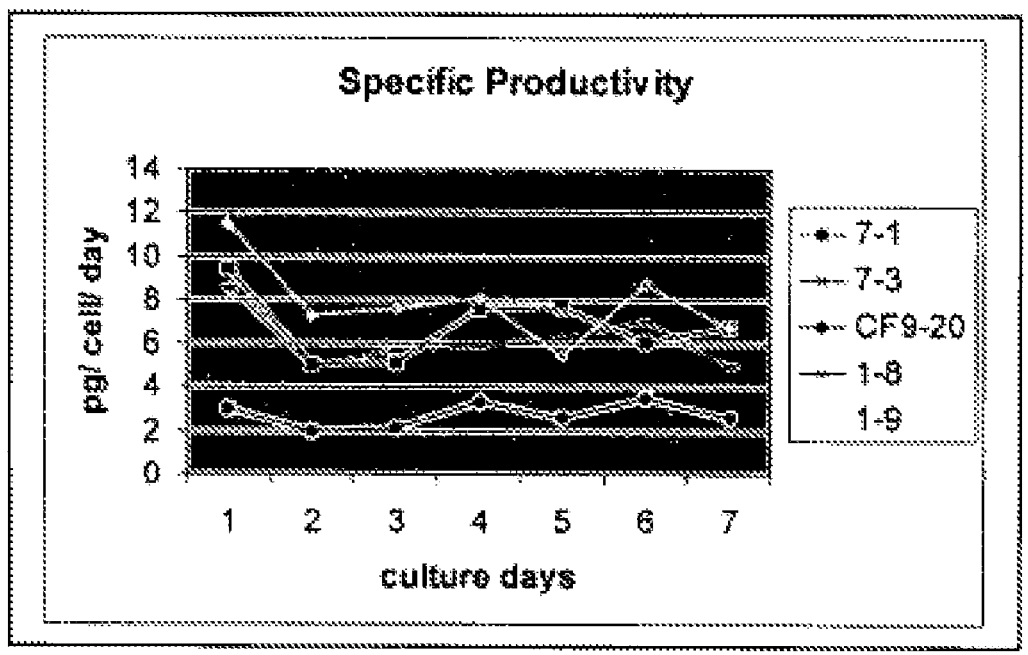
FIG. 4 is an illustration of overexpression of bikunin in clones super transfected with Hsp70. All clones except CF9-

The effect of chaperone proteins on bikunin expression is shown in FIGS. 3 and 4. The control cell line (CF9-20) expresses Bikunin but does not express any of chaperone proteins. The effect of calnexin, calreticulin, and Erp57 on bikunin expression is further summarized in Table 1.

TABLE 1

Overall Bikunin production levels are 2-4 fold higher in clones that have been super transfected with a chaperone

| Clone | Bikunin Increase Relative to Control | Chaperone |
| --- | --- | --- |
| X4/14:5 | 2-4 | CNX |
| X4/14:30 | 2-4 | CNX |
| X4/19:62 | 2-4 | ERp57 |
| T4/13:22 | 1.5-2 | CRT |

Fold activity measurements are relative to a control cell line that expresses Bikunin but does not express any of the chaperone proteins. Cells were grown in serum free media in shake flask cultures.

Example 3

Recombinant Factor VIII Production is Increased in BHK Cells after Transfection with ER Chaperones Stable Factor VIII producing cells (MWCB1) (U.S. Pat. No. 4,965,199; ATCC No. CRL 8544) were transfected with chaperone expression vectors in addition to pPUR, a vector containing puromycin-resistant gene, in a 10:1 ratio. Approximately 4×10$^6$ MWCB1 cells were transfected with a total of 5 μg of DNA using the DMRIE-C reagent and OPTI-MEM medium (Life Technology, MD) in 6-well plates. Three days post transfection, 100,000 cells were seeded in 6-well plates and then selected in the presence of 1-2 μg/ml puromycin with OPTI-MEM medium containing 2% FBS for 2 weeks. Puromycin resistant colonies were manually picked and seeded into 96 well plates and expanded without the presence of drug. Individual clonal populations were screened for Factor VIII production using a COATEST kit (Chromogenix, Italy) according to manufacturer's instructions. The high producing clones were sequentially expanded from the 6 well dish, to T75 flask, followed by shake flask stage for stability and productivity tests. The Calnexin (CNX), Calreticulin (CRT), Erp57, Hsp40 and Hsp70 chaperones were then transfected into cells individually or in combinations of two. A significant 2 to 3 fold increase of productivity of Factor VIII was observed in clones transfected with CNX, CRT and Erp57, Hsp70, and Hsp40 while the empty vector control (PCI-Neo) showed no difference compared to the parent MWCB1 cells (Table 2).

TABLE 2

Recombinant Factor VIII productivity in clones

| | Factor VIII (U/ml) | Fold of Inc (SPR) |
| --- | --- | --- |
| MWCB1(27000JC) | 0.11 | 1.00 |
| PCI-Neo + pPUR | 0.09 | 1.00 |
| CNX + pPUR | 0.31 | 2.88 |
| CRT + pPUR | 0.13 | 1.25 |
| Erp57 + pPUR | 0.05 | 0.91 |
| CRT, Erp57 + pPUR | 0.29 | 2.50 |
| Hsp70 + pPUR | 0.37 | 2.50 |
| Hsp40 + pPUR | 0.11 | 1.00 |
| Hsp70, 40 + pPUR | 0.28 | 1.66 |

Cells were seeded at 1 × 10$^6$ per ml, total 15 ml in shake flask 2-day

Example 4

Co-Expression of BiP and PDI does not Enhance the Expression of Factor VIII and Anti-TNF Antibody in BHK and CHO Cells Recombinant CHO cells (as described in Example 2) expressing high levels of bikunin, and recombinant BHK cells (as described in Example 3) expressing high levels of recombinant Factor VIII (rFVIII) were super-transfected with pHyg (plasmid conferring hygromycin resistance) and pBiP. The transfection conditions and selection conditions were same as in Example 2. After selection in hygromycin and limiting dilution cloning, clones were evaluated for productivity for bikunin and rFVIII activity. No significant difference in the specific productivity of clones derived from cells transfected only with the control vector (pHyg) and clones derived from cells transfected with pBiP.

Example 5

Transfection of IL2SA-Producing Clone with Glutamine Synthetase (GS) and Hsp70

IL2SA (IL2 selective agonist; U.S. Pat. No. 6,348,192, included herein by reference in its entirety) producing CHO cell line, 49-19-H42 (a clonal variant of ATCC deposit PTA-8), was co-transfected with PCI-GS and PCI-neo-Hsp70. 4×10$^6$ cells were transfected with 2.5 μg of plasmid DNA using DMRIE-C reagents and OPTI-MEM medium (Life Technology, MD) in 6-well plates according to manufacturer's instructions. Three days after transfection, cells were seeded in 150-mm and 96 well plates and then selected in the presence of 10 μM MSX (methionine sulfoxinmine) and 250 μg/ml G418 with DME:F12 (1:1) medium deficient in glutamine containing 2% dialyzed FBS for 2 weeks. Single cell colonies were picked and re-seeded in 96 wells. The clones were selected for another week with increased concentrations of MSX (20 μM) and G418 (400 μg/ml). A pool is generated from a 150-mm plate after 3 weeks' selection. The pool and clones were gradually expanded to shake flasks and screened for IL2 productivity using ELISA. The expression of GS and Hsp70 proteins were confirmed by FACS analysis using a flow cytometer. The "GS positive" cells were cultured in a glutamine-free medium supplement with 5.6 mM glutamate and 4 g/L glucose. The doubling time of these clones varied from 24 to 48 hr. A comparison of the productivity of the parent and clones is shown in Table 3. A 2-4 fold increase in overall titer and a 2-3 fold increase in specific productivity was observed in all the single cell clones when compared against either the pool or the parental line.

TABLE 3

Productivity of IL2SA producing cells

| | Titer (μg/ml) | Cell density ($10^6$/ml) | SPR (pg/c/d) | GS | Hsp70 |
|---|---|---|---|---|---|
| 49-19H42 parent line | 18.78 | 3.51 | 2.67 | (−) | (−) |
| 49-19H42 GShsp70-SC#12 | 33.87 | 2.63 | 6.44 | +++ | +++ |
| 49-19H42 GShsp70-SC#14 | 22.08 | 1.83 | 6.03 | +++ | +++ |
| 49-19H42 GShsp70-SC#17 | 64.00 | 3.05 | 10.50 | +++ | +++ |
| 49-19H42 GShsp70-pool | 10.59 | 1.74 | 3.04 | +++ | + |

Cells were seeded at 1 million per ml at day 0 in 15 ml of complete (for the parental line) or glutamine-free medium. Samples were taken at 2 day after seeding and analyzed using ELISA. For GS and Hsp70 expression, cells were fixed with 70% EtOH, labeled with proper antibodies, and analyzed by FACS.
+++ = all cells expressed GS or Hsp70;
+ = 30% of cells expressed GS or Hsp70;
(−) = no expression.

REFERENCES (1) Wunderlich, M.; Glockshuber, R. In vivo control of redox potential during protein folding catalyzed by bacterial protein disulfide-isomerase (DsbA). *J. Biol. Chem.* 1993, 268, 24547-24550.
(2) Glockshuber, R.; Wunderlich, M.; Skerra, A.; Rudolph, R. Increasing the yield of disulfide-bridged heterologous proteins secreted from transgenic microorganisms. Eur. Pat. No. 92-106978 920423 1995.
(3) Tuite, M. F.; Freedman, R. B.; Schultz, L. D.; Ellis, R. W.; Markus, H. Z.; Montgomery, D. L. Method for increasing production of disulfide bonded recombinant proteins by *saccharomyces cerevisiae*. Aust. Pat. No. AU679448B2 1997.
(4) Ostermeier, M.; De Sutter, K.; Georgiou, G. Eukaryotic protein disulfide isomerase complements *Escherichia coli* dsbA mutants and increases the yield of a heterologous secreted protein with disulfide bonds. *J. Biol. Chem.* 1996, 271, 10616-10622.
(5) Shusta, E. V.; Raines, R. T.; Pluckthun, A.; Wittrup, K. D. Increasing the secretory capacity of *Saccharomyces cerevisiae* for production of single-chain antibody fragments. *Nat. Bio-technol.* 1998, 16, 773-777.
(6) Robinson, A. S.; Hines, V.; Wittrup, K. D. Protein disulfide isomerase overexpression increases secretion of foreign proteins in *Saccharomyces cerevisiae*. *Biotechnology (N.Y.)* 1994, 12, 381-384.
(7) Dunn, A.; Luz, J. M.; Natalia, D.; Gamble, J. A.; Freedman, R. B.; Tuite, M. F. Protein disulphide isomerase (PDI) is required for the secretion of a native disulphide-bonded protein from *Saccharomyces cerevisiae*. *Biochem. Soc. Trans.* 1995, 23, 78S.
(8) Hsu, T. A.; Watson, S.; Eiden, J. J.; Betenbaugh, M. J. Rescue of immunoglobulins from insolubility is facilitated by PDI in the baculovirus expression system. *Protein Expr. Purif.* 1996, 7, 281-288.
(9) Hsu, T. A.; Betenbaugh, M. J. Co-expression of molecular chaperone BiP improves immunoglobulin solubility and IgG secretion from *Trichoplusia* in insect cells. *Biotechnol. Prog.* 1997, 13, 96-104.
(10) Hsu, T. A.; Eiden, J. J.; Bourgarel, P.; Meo, T.; Betenbaugh, M. J. Effects of co-expressing chaperone BiP on functional antibody production in the baculovirus system. *Protein Expr. Purif.* 1994, 5, 595-603.
(11) Ailor, E.; Betenbaugh, M. J. Overexpression of a cytosolic chaperone to improve solubility and secretion of a recombinant IgG protein in insect cells. *Biotechnol. Bioeng.* 1998, 58, 196-203.
(12) Ailor, E.; Betenbaugh, M. J. Modifying secretion and post-translational processing in insect cells. *Curr. Opin. Biotechnol.* 1999, 10, 142-145.
(13) Davis, R., Schooley, K., Rasmussen, B., Thomas, J., Reddy, P. Effect of PDI Overexpression on Recombinant Protein Secretion in CHO Cells. Biotechnol. Prog. 2000, 16, 736-743.
(14) Dorner, A. J.; Wasley, L. C.; Raney, P.; Haugejorden, S.; Green, M.; Kaufman, R. J. The stress response in Chinese hamster ovary cells. Regulation of ERp72 and protein disulfide isomerase expression and secretion. *J. Biol. Chem.* 1990, 265, 22029-22034.
(15) Dorner, A. J.; Wasley, L. C.; Kaufman, R. J. Overexpression of GRP78 mitigates stress induction of glucose regulated proteins and blocks secretion of selective proteins in Chinese hamster ovary cells. *EMBO J.* 1992, 11, 1563-1571.
(16) Current Protocols in Molecular Biology, 2003, John Wiley & Sons, Inc.

What is claimed:

1. A mammalian host cell for enhanced expression of a recombinant protein product, said mammalian cell having genetic material coding for expression of said recombinant protein product and transformed with at least one expression vector comprising DNA encoding chaperone proteins calreticulin and Erp57 wherein said recombinant protein is Factor VIII or fragment thereof.

2. The mammalian host cell according to claim 1, wherein the recombinant protein product is secreted.

3. The mammalian host cell according to claim 2, wherein the genetic material coding for expression of said recombinant protein product is integrated into host cell DNA.

4. The mammalian host cell according to claim 3, further transformed with an expression vector comprising DNA encoding a glutamine synthetase protein.

* * * * *

SEQUENCE LISTING

<160> NUMBER OF SEQ ID NOS: 22

<210> SEQ ID NO 1
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 1
atgaattccg ggaggctaga gatcatgg                                      28

<210> SEQ ID NO 2
<211> LENGTH: 28
<212> TYPE: DNA
<213> ORGANISM: Artificial sequence
<220> FEATURE:
<223> OTHER INFORMATION: synthetic oligonucleotide

```
<400> SEQUENCE: 2
attctagatg cagggggagga gggagaag                                           28

<210> SEQ ID NO 3
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 3
atgaattccc gccatgctgc tatccgtg                                            28

<210> SEQ ID NO 4
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 4
attctagact ggaggcaggc ctctctac                                            28

<210> SEQ ID NO 5
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 5
atgaattcct ccgcagtccc agccgagc                                            28

<210> SEQ ID NO 6
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 6
attctagact ctcggccctg agaggtaa                                            28

<210> SEQ ID NO 7
<211> LENGTH: 1856
<212> TYPE: DNA
<213> ORGANISM: Homo sapiens
<220> FEATURE:
<221> NAME/KEY: CDS
<222> LOCATION: (23)..(1801)

<400> SEQUENCE: 7
gaattccggg aggctagaga tc atg gaa ggg aag tgg ttg ctg tgt atg tta        52
                         Met Glu Gly Lys Trp Leu Leu Cys Met Leu
                           1               5                  10 ctg gtg ctt gga act gct att gtt gag gct cat gat gga cat gat gat       100
Leu Val Leu Gly Thr Ala Ile Val Glu Ala His Asp Gly His Asp Asp
             15                  20                  25 gat gtg att gat att gag gat gac ctt gac gat gtc att gaa gag gta       148
Asp Val Ile Asp Ile Glu Asp Asp Leu Asp Asp Val Ile Glu Glu Val
         30                  35                  40 gaa gac tca aaa cca gat acc act gct cct cct tca tct ccc aag gtt       196
Glu Asp Ser Lys Pro Asp Thr Thr Ala Pro Pro Ser Ser Pro Lys Val
     45                  50                  55
```

| | |
|---|---|
| act tac aaa gct cca gtt cca aca ggg gaa gta tat ttt gct gat tct<br>Thr Tyr Lys Ala Pro Val Pro Thr Gly Glu Val Tyr Phe Ala Asp Ser<br>    60                        65                        70 | 244 |
| ttt gac aga gga act ctg tca ggg tgg att tta tcc aaa gcc aag aaa<br>Phe Asp Arg Gly Thr Leu Ser Gly Trp Ile Leu Ser Lys Ala Lys Lys<br>75                        80                        85                        90 | 292 |
| gac gat acc gat gat gaa att gcc aaa tat gat gga aag tgg gag gta<br>Asp Asp Thr Asp Asp Glu Ile Ala Lys Tyr Asp Gly Lys Trp Glu Val<br>                        95                        100                      105 | 340 |
| gag gaa atg aag gag tca aag ctt cca ggt gat aaa gga ctt gtg ttg<br>Glu Glu Met Lys Glu Ser Lys Leu Pro Gly Asp Lys Gly Leu Val Leu<br>              110                        115                      120 | 388 |
| atg tct cgg gcc aag cat cat gcc atc tct gct aaa ctg aac aag ccc<br>Met Ser Arg Ala Lys His His Ala Ile Ser Ala Lys Leu Asn Lys Pro<br>        125                        130                      135 | 436 |
| ttc ctg ttt gac acc aag cct ctc att gtt cag tat gag gtt aat ttc<br>Phe Leu Phe Asp Thr Lys Pro Leu Ile Val Gln Tyr Glu Val Asn Phe<br>    140                        145                      150 | 484 |
| caa aat gga ata gaa tgt ggt ggt gcc tat gtg aaa ctg ctt tct aaa<br>Gln Asn Gly Ile Glu Cys Gly Gly Ala Tyr Val Lys Leu Leu Ser Lys<br>155                        160                        165                        170 | 532 |
| aca cca gaa ctc aac ctg gat cag ttc cat gac aag acc cct tat acg<br>Thr Pro Glu Leu Asn Leu Asp Gln Phe His Asp Lys Thr Pro Tyr Thr<br>                    175                        180                      185 | 580 |
| att atg ttt ggt cca gat aaa tgt gga gag gac tat aaa ctg cac ttc<br>Ile Met Phe Gly Pro Asp Lys Cys Gly Glu Asp Tyr Lys Leu His Phe<br>              190                        195                      200 | 628 |
| atc ttc cga cac aaa aac ccc aaa acg ggt atc tat gaa gaa aaa cat<br>Ile Phe Arg His Lys Asn Pro Lys Thr Gly Ile Tyr Glu Glu Lys His<br>        205                        210                      215 | 676 |
| gct aag agg cca gat gca gat ctg aag acc tat ttt act gat aag aaa<br>Ala Lys Arg Pro Asp Ala Asp Leu Lys Thr Tyr Phe Thr Asp Lys Lys<br>    220                        225                      230 | 724 |
| aca cat ctt tac aca cta atc ttg aat cca gat aat agt ttt gaa ata<br>Thr His Leu Tyr Thr Leu Ile Leu Asn Pro Asp Asn Ser Phe Glu Ile<br>235                        240                        245                        250 | 772 |
| ctg gtt gac caa tct gtg gtg aat agt gga aat ctg ctc aat gac atg<br>Leu Val Asp Gln Ser Val Val Asn Ser Gly Asn Leu Leu Asn Asp Met<br>                    255                        260                      265 | 820 |
| act cct cct gta aat cct tca cgt gaa att gag gac cca gaa gac cgg<br>Thr Pro Pro Val Asn Pro Ser Arg Glu Ile Glu Asp Pro Glu Asp Arg<br>              270                        275                      280 | 868 |
| aag ccc gag gat tgg gat gaa aga cca aaa atc cca gat cca gaa gct<br>Lys Pro Glu Asp Trp Asp Glu Arg Pro Lys Ile Pro Asp Pro Glu Ala<br>        285                        290                      295 | 916 |
| gtc aag cca gat gac tgg gat gaa gat gcc cct gct aag att cca gat<br>Val Lys Pro Asp Asp Trp Asp Glu Asp Ala Pro Ala Lys Ile Pro Asp<br>300                        305                        310 | 964 |
| gaa gag gcc aca aaa ccc gaa ggc tgg tta gat gat gag cct gag tac<br>Glu Glu Ala Thr Lys Pro Glu Gly Trp Leu Asp Asp Glu Pro Glu Tyr<br>315                        320                        325                      330 | 1012 |
| gta cct gat cca gac gca gag aaa cct gag gat tgg gat gaa gac atg<br>Val Pro Asp Pro Asp Ala Glu Lys Pro Glu Asp Trp Asp Glu Asp Met<br>                    335                        340                      345 | 1060 |
| gat gga gaa tgg gag gct cct cag att gcc aac cct aga tgt gag tca<br>Asp Gly Glu Trp Glu Ala Pro Gln Ile Ala Asn Pro Arg Cys Glu Ser<br>              350                        355                      360 | 1108 |
| gct cct gga tgt ggt gtc tgg cag cga cct gtg att gac aac ccc aat<br>Ala Pro Gly Cys Gly Val Trp Gln Arg Pro Val Ile Asp Asn Pro Asn<br>        365                        370                      375 | 1156 |

```
tat aaa ggc aaa tgg aag cct cct atg att gac aat ccc agt tac cag      1204
Tyr Lys Gly Lys Trp Lys Pro Pro Met Ile Asp Asn Pro Ser Tyr Gln
    380                 385                 390 gga atc tgg aaa ccc agg aaa ata cca aat cca gat ttc ttt gaa gat      1252
Gly Ile Trp Lys Pro Arg Lys Ile Pro Asn Pro Asp Phe Phe Glu Asp
395                 400                 405                 410 ctg gaa cct ttc aga atg act cct ttt agt gct att ggt ttg gag ctg      1300
Leu Glu Pro Phe Arg Met Thr Pro Phe Ser Ala Ile Gly Leu Glu Leu
                415                 420                 425 tgg tcc atg acc tct gac att ttt ttt gac aac ttt atc att tgt gct      1348
Trp Ser Met Thr Ser Asp Ile Phe Phe Asp Asn Phe Ile Ile Cys Ala
            430                 435                 440 gat cga aga ata gtt gat gat tgg gcc aat gat gga tgg ggc ctg aag      1396
Asp Arg Arg Ile Val Asp Asp Trp Ala Asn Asp Gly Trp Gly Leu Lys
        445                 450                 455 aaa gct gct gat ggg gct gct gag cca ggc gtt gtg ggg cag atg atc      1444
Lys Ala Ala Asp Gly Ala Ala Glu Pro Gly Val Val Gly Gln Met Ile
    460                 465                 470 gag gca gct gaa gag cgc ccg tgg ctg tgg gta gtc tat att cta act      1492
Glu Ala Ala Glu Glu Arg Pro Trp Leu Trp Val Val Tyr Ile Leu Thr
475                 480                 485                 490 gta gcc ctt cct gtg ttc ctg gtt atc ctc ttc tgc tgt tct gga aag      1540
Val Ala Leu Pro Val Phe Leu Val Ile Leu Phe Cys Cys Ser Gly Lys
                495                 500                 505 aaa cag acc agt ggt atg gag tat aag aaa act gat gca cct caa ccg      1588
Lys Gln Thr Ser Gly Met Glu Tyr Lys Lys Thr Asp Ala Pro Gln Pro
            510                 515                 520 gat gtg aag gaa gag gaa gag aag gaa gag gaa aag gac aag gga          1636
Asp Val Lys Glu Glu Glu Glu Lys Glu Glu Glu Lys Asp Lys Gly
        525                 530                 535 gat gag gag gag gaa gga gaa gag aaa ctt gaa gag aaa cag aaa agt      1684
Asp Glu Glu Glu Glu Gly Glu Glu Lys Leu Glu Glu Lys Gln Lys Ser
    540                 545                 550 gat gct gaa gaa gat ggt ggc act gtc agt caa gag gag gaa gac aga      1732
Asp Ala Glu Glu Asp Gly Gly Thr Val Ser Gln Glu Glu Glu Asp Arg
555                 560                 565                 570 aaa cct aaa gca gag gag gat gaa att ttg aac aga tca cca aga aac      1780
Lys Pro Lys Ala Glu Glu Asp Glu Ile Leu Asn Arg Ser Pro Arg Asn
                575                 580                 585 aga aag cca cga aga gag tga acaatctta agagcttgat ctgtgatttc          1831
Arg Lys Pro Arg Arg Glu
            590 ttctccctcc tccctgcat ctaga                                           1856

<210> SEQ ID NO 8
<211> LENGTH: 592
<212> TYPE: PRT
<213> ORGANISM: Homo sapiens

<400> SEQUENCE: 8

Met Glu Gly Lys Trp Leu Leu Cys Met Leu Leu Val Leu Gly Thr Ala
1               5                   10                  15

Ile Val Glu Ala His Asp Gly His Asp Asp Val Ile Asp Ile Glu
            20                  25                  30

Asp Asp Leu Asp Asp Val Ile Glu Glu Val Glu Asp Ser Lys Pro Asp
        35                  40                  45

Thr Thr Ala Pro Pro Ser Ser Pro Lys Val Tyr Lys Ala Pro Val
    50                  55                  60

Pro Thr Gly Glu Val Tyr Phe Ala Asp Ser Phe Asp Arg Gly Thr Leu
65              70                  75                  80
```

-continued

```
Ser Gly Trp Ile Leu Ser Lys Ala Lys Lys Asp Asp Thr Asp Asp Glu
                85                  90                  95

Ile Ala Lys Tyr Asp Gly Lys Trp Glu Val Glu Glu Met Lys Glu Ser
            100                 105                 110

Lys Leu Pro Gly Asp Lys Gly Leu Val Leu Met Ser Arg Ala Lys His
        115                 120                 125

His Ala Ile Ser Ala Lys Leu Asn Lys Pro Phe Leu Phe Asp Thr Lys
    130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
            180                 185                 190

Lys Cys Gly Glu Asp Tyr Lys Leu His Phe Ile Phe Arg His Lys Asn
        195                 200                 205

Pro Lys Thr Gly Ile Tyr Glu Glu Lys His Ala Lys Arg Pro Asp Ala
    210                 215                 220

Asp Leu Lys Thr Tyr Phe Thr Asp Lys Lys Thr His Leu Tyr Thr Leu
225                 230                 235                 240

Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
            260                 265                 270

Ser Arg Glu Ile Glu Asp Pro Glu Asp Arg Lys Pro Glu Asp Trp Asp
        275                 280                 285

Glu Arg Pro Lys Ile Pro Asp Pro Glu Ala Val Lys Pro Asp Asp Trp
    290                 295                 300

Asp Glu Asp Ala Pro Ala Lys Ile Pro Asp Glu Glu Ala Thr Lys Pro
305                 310                 315                 320

Glu Gly Trp Leu Asp Asp Glu Pro Glu Tyr Val Pro Asp Pro Asp Ala
                325                 330                 335

Glu Lys Pro Glu Asp Trp Asp Glu Asp Met Asp Gly Glu Trp Glu Ala
            340                 345                 350

Pro Gln Ile Ala Asn Pro Arg Cys Glu Ser Ala Pro Gly Cys Gly Val
        355                 360                 365

Trp Gln Arg Pro Val Ile Asp Asn Pro Asn Tyr Lys Gly Lys Trp Lys
    370                 375                 380

Pro Pro Met Ile Asp Asn Pro Ser Tyr Gln Gly Ile Trp Lys Pro Arg
385                 390                 395                 400

Lys Ile Pro Asn Pro Asp Phe Phe Glu Asp Leu Glu Pro Phe Arg Met
                405                 410                 415

Thr Pro Phe Ser Ala Ile Gly Leu Glu Leu Trp Ser Met Thr Ser Asp
            420                 425                 430

Ile Phe Phe Asp Asn Phe Ile Ile Cys Ala Asp Arg Arg Ile Val Asp
        435                 440                 445

Asp Trp Ala Asn Asp Gly Trp Gly Leu Lys Lys Ala Ala Asp Gly Ala
    450                 455                 460

Ala Glu Pro Gly Val Val Gly Gln Met Ile Glu Ala Ala Glu Glu Arg
465                 470                 475                 480

Pro Trp Leu Trp Val Val Tyr Ile Leu Thr Val Ala Leu Pro Val Phe
                485                 490                 495

Leu Val Ile Leu Phe Cys Cys Ser Gly Lys Lys Gln Thr Ser Gly Met
```

```
                      500                 505                  510
Glu Tyr Lys Lys Thr Asp Ala Pro Gln Pro Asp Val Lys Glu Glu Glu
            515                 520                 525

Glu Glu Lys Glu Glu Lys Asp Lys Gly Asp Glu Glu Glu Gly
        530                 535                 540

Glu Glu Lys Leu Glu Glu Lys Gln Lys Ser Asp Ala Glu Glu Asp Gly
545                 550                 555                 560

Gly Thr Val Ser Gln Glu Glu Asp Arg Lys Pro Lys Ala Glu Glu
                565                 570                 575

Asp Glu Ile Leu Asn Arg Ser Pro Arg Asn Arg Lys Pro Arg Arg Glu
            580                 585                 590

<210> SEQ ID NO 9
<211> LENGTH: 1287
<212> TYPE: DNA
<213> ORGANISM: Homo sapiens
<220> FEATURE:
<221> NAME/KEY: CDS
<222> LOCATION: (12)..(1265)

<400> SEQUENCE: 9
gaattcccgc c atg ctg cta tcc gtg ccg ctg ctg ctc ggc ctc ctc ggc          50
             Met Leu Leu Ser Val Pro Leu Leu Leu Gly Leu Leu Gly
               1               5                  10 ctg gcc gtc gcc gag cct gcc gtc tac ttc aag gag cag ttt ctg gac          98
Leu Ala Val Ala Glu Pro Ala Val Tyr Phe Lys Glu Gln Phe Leu Asp
     15                  20                  25 gga gac ggg tgg act tcc cgc tgg atc gaa tcc aaa cac aag tca gat         146
Gly Asp Gly Trp Thr Ser Arg Trp Ile Glu Ser Lys His Lys Ser Asp
 30                  35                  40                  45 ttt ggc aaa ttc gtt ctc agt tcc ggc aag ttc tac ggt gac gag gag         194
Phe Gly Lys Phe Val Leu Ser Ser Gly Lys Phe Tyr Gly Asp Glu Glu
                 50                  55                  60 aaa gat aaa ggt ttg cag aca agc cag gat gca cgc ttt tat gct ctg         242
Lys Asp Lys Gly Leu Gln Thr Ser Gln Asp Ala Arg Phe Tyr Ala Leu
             65                  70                  75 tcg gcc agt ttc gag cct ttc agc aac aaa ggc cag acg ctg gtg gtg         290
Ser Ala Ser Phe Glu Pro Phe Ser Asn Lys Gly Gln Thr Leu Val Val
         80                  85                  90 cag ttc acg gtg aaa cat gag cag aac atc gac tgt ggg ggc ggc tat         338
Gln Phe Thr Val Lys His Glu Gln Asn Ile Asp Cys Gly Gly Gly Tyr
     95                 100                 105 gtg aag ctg ttt cct aat agt ttg gac cag aca gac atg cac gga gac         386
Val Lys Leu Phe Pro Asn Ser Leu Asp Gln Thr Asp Met His Gly Asp
110                 115                 120                 125 tca gaa tac aac atc atg ttt ggt ccc gac atc tgt ggc cct ggc acc         434
Ser Glu Tyr Asn Ile Met Phe Gly Pro Asp Ile Cys Gly Pro Gly Thr
                130                 135                 140 aag aag gtt cat gtc atc ttc aac tac aag ggc aag aac gtg ctg atc         482
Lys Lys Val His Val Ile Phe Asn Tyr Lys Gly Lys Asn Val Leu Ile
            145                 150                 155 aac aag gac atc cgt tgc aag gat gat gag ttt aca cac ctg tac aca         530
Asn Lys Asp Ile Arg Cys Lys Asp Asp Glu Phe Thr His Leu Tyr Thr
        160                 165                 170 ctg att gtg cgg cca gac aac acc tat gag gtg aag att gac aac agc         578
Leu Ile Val Arg Pro Asp Asn Thr Tyr Glu Val Lys Ile Asp Asn Ser
    175                 180                 185 cag gtg gag tcc ggc tcc ttg gaa gac gat tgg gac ttc ctg cca ccc         626
Gln Val Glu Ser Gly Ser Leu Glu Asp Asp Trp Asp Phe Leu Pro Pro
190                 195                 200                 205
```

```
                                      -continued
aag aag ata aag gat cct gat gct tca aaa ccg gaa gac tgg gat gag    674
Lys Lys Ile Lys Asp Pro Asp Ala Ser Lys Pro Glu Asp Trp Asp Glu
            210                 215                 220 cgg gcc aag atc gat gat ccc aca gac tcc aag cct gag gac tgg gac    722
Arg Ala Lys Ile Asp Asp Pro Thr Asp Ser Lys Pro Glu Asp Trp Asp
        225                 230                 235 aag ccc gag cat atc cct gac cct gat gct aag aag ccc gag gac tgg    770
Lys Pro Glu His Ile Pro Asp Pro Asp Ala Lys Lys Pro Glu Asp Trp
    240                 245                 250 gat gaa gag atg gac gga gag tgg gaa ccc cca gtg att cag aac cct    818
Asp Glu Glu Met Asp Gly Glu Trp Glu Pro Pro Val Ile Gln Asn Pro
255                 260                 265 gag tac aag ggt gag tgg aag ccc cgg cag atc gac aac cca gat tac    866
Glu Tyr Lys Gly Glu Trp Lys Pro Arg Gln Ile Asp Asn Pro Asp Tyr
270                 275                 280                 285 aag ggc act tgg atc cac cca gaa att gac aac ccc gag tat tct ccc    914
Lys Gly Thr Trp Ile His Pro Glu Ile Asp Asn Pro Glu Tyr Ser Pro
                290                 295                 300 gat ccc agt atc tat gcc tat gat aac ttt ggc gtg ctg ggc ctg gac    962
Asp Pro Ser Ile Tyr Ala Tyr Asp Asn Phe Gly Val Leu Gly Leu Asp
            305                 310                 315 ctc tgg cag gtc aag tct ggc acc atc ttt gac aac ttc ctc atc acc   1010
Leu Trp Gln Val Lys Ser Gly Thr Ile Phe Asp Asn Phe Leu Ile Thr
        320                 325                 330 aac gat gag gca tac gct gag gag ttt ggc aac gag acg tgg ggc gta   1058
Asn Asp Glu Ala Tyr Ala Glu Glu Phe Gly Asn Glu Thr Trp Gly Val
    335                 340                 345 aca aag gca gca gag aaa caa atg aag gac aaa cag gac gag gag cag   1106
Thr Lys Ala Ala Glu Lys Gln Met Lys Asp Lys Gln Asp Glu Glu Gln
350                 355                 360                 365 agg ctt aag gag gag gaa gaa gac aag aaa cgc aaa gag gag gag gag   1154
Arg Leu Lys Glu Glu Glu Glu Asp Lys Lys Arg Lys Glu Glu Glu Glu
                370                 375                 380 gca gag gac aag gag gat gat gag gac aaa gat gag gat gag gag gat   1202
Ala Glu Asp Lys Glu Asp Asp Glu Asp Lys Asp Glu Asp Glu Glu Asp
            385                 390                 395 gag gag gac aag gag gaa gat gag gag gaa gat gtc ccc ggc cag gcc   1250
Glu Glu Asp Lys Glu Glu Asp Glu Glu Glu Asp Val Pro Gly Gln Ala
        400                 405                 410 aag gac gag ctg tag agaggcctgc ctccagtcta ga                      1287
Lys Asp Glu Leu
        415

<210> SEQ ID NO 10
<211> LENGTH: 417
<212> TYPE: PRT
<213> ORGANISM: Homo sapiens

<400> SEQUENCE: 10

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
```

```
                85                  90                  95
Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
    370                 375                 380

Lys Glu Asp Asp Glu Asp Lys Asp Glu Asp Glu Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 11
<211> LENGTH: 1696
<212> TYPE: DNA
<213> ORGANISM: Homo sapiens
<220> FEATURE:
<221> NAME/KEY: CDS
<222> LOCATION: (65)..(1582)

<400> SEQUENCE: 11
gaattcctcc gcagtcccag ccgagccgcg acccttccgg ccgtcccac cccacctcgc      60 cgcc atg cgc ctc cgc cgc cta gcg ctg ttc ccg ggt gtg gcg ctg ctt    109
     Met Arg Leu Arg Arg Leu Ala Leu Phe Pro Gly Val Ala Leu Leu
     1               5                  10                  15
```

| | | | | | | | | | | | | | | |
|---|---|---|---|---|---|---|---|---|---|---|---|---|---|---|
| ctt | gcc | gcg | gcc | cgc | ctc | gcc | gct | gcc | tcc | gac | gtg | cta | gaa | ctc | acg | 157 |
| Leu | Ala | Ala | Ala | Arg | Leu | Ala | Ala | Ala | Ser | Asp | Val | Leu | Glu | Leu | Thr | |
| | | | 20 | | | | | 25 | | | | | 30 | | | |

| gac | gac | aac | ttc | gag | agt | cgc | atc | tcc | gac | acg | ggc | tct | gcg | ggc | ctc | 205 |
| Asp | Asp | Asn | Phe | Glu | Ser | Arg | Ile | Ser | Asp | Thr | Gly | Ser | Ala | Gly | Leu | |
| | | | 35 | | | | | 40 | | | | | 45 | | | |

| atg | ctc | gtc | gag | ttc | ttc | gct | ccc | tgg | tgt | gga | cac | tgc | aag | aga | ctt | 253 |
| Met | Leu | Val | Glu | Phe | Phe | Ala | Pro | Trp | Cys | Gly | His | Cys | Lys | Arg | Leu | |
| 50 | | | | | 55 | | | | | 60 | | | | | | |

| gca | cct | gag | tat | gaa | gct | gca | gct | acc | aga | tta | aaa | gga | ata | gtc | cca | 301 |
| Ala | Pro | Glu | Tyr | Glu | Ala | Ala | Ala | Thr | Arg | Leu | Lys | Gly | Ile | Val | Pro | |
| 65 | | | | | 70 | | | | | 75 | | | | | | |

| tta | gca | aag | gtt | gat | tgc | act | gcc | aac | act | aac | acc | tgt | aat | aaa | tat | 349 |
| Leu | Ala | Lys | Val | Asp | Cys | Thr | Ala | Asn | Thr | Asn | Thr | Cys | Asn | Lys | Tyr | |
| 80 | | | | 85 | | | | | 90 | | | | | 95 | | |

| gga | gtc | agt | gga | tat | cca | acc | ctg | aag | ata | ttt | aga | gat | ggt | gaa | gaa | 397 |
| Gly | Val | Ser | Gly | Tyr | Pro | Thr | Leu | Lys | Ile | Phe | Arg | Asp | Gly | Glu | Glu | |
| | | | 100 | | | | | 105 | | | | | 110 | | | |

| gca | ggt | gct | tat | gat | gga | cct | agg | act | gct | gat | gga | att | gtc | agc | cac | 445 |
| Ala | Gly | Ala | Tyr | Asp | Gly | Pro | Arg | Thr | Ala | Asp | Gly | Ile | Val | Ser | His | |
| | | | 115 | | | | | 120 | | | | | 125 | | | |

| ttg | aag | aag | cag | gca | gga | cca | gct | tca | gtg | cct | ctc | agg | act | gag | gaa | 493 |
| Leu | Lys | Lys | Gln | Ala | Gly | Pro | Ala | Ser | Val | Pro | Leu | Arg | Thr | Glu | Glu | |
| | | | 130 | | | | | 135 | | | | | 140 | | | |

| gaa | ttt | aag | aaa | ttc | att | agt | gat | aaa | gat | gcc | tct | ata | gta | ggt | ttt | 541 |
| Glu | Phe | Lys | Lys | Phe | Ile | Ser | Asp | Lys | Asp | Ala | Ser | Ile | Val | Gly | Phe | |
| | | 145 | | | | | 150 | | | | | 155 | | | | |

| ttc | gat | gat | tca | ttc | agt | gag | gct | cac | tcc | gag | ttc | cta | aaa | gca | gcc | 589 |
| Phe | Asp | Asp | Ser | Phe | Ser | Glu | Ala | His | Ser | Glu | Phe | Leu | Lys | Ala | Ala | |
| 160 | | | | | 165 | | | | | 170 | | | | | 175 | |

| agc | aac | ttg | agg | gat | aac | tac | cga | ttt | gca | cat | acg | aat | gtt | gag | tct | 637 |
| Ser | Asn | Leu | Arg | Asp | Asn | Tyr | Arg | Phe | Ala | His | Thr | Asn | Val | Glu | Ser | |
| | | | 180 | | | | | 185 | | | | | 190 | | | |

| ctg | gtg | aac | gag | tat | gat | gat | aat | gga | gag | ggt | atc | atc | tta | ttt | cgt | 685 |
| Leu | Val | Asn | Glu | Tyr | Asp | Asp | Asn | Gly | Glu | Gly | Ile | Ile | Leu | Phe | Arg | |
| | | | 195 | | | | | 200 | | | | | 205 | | | |

| cct | tca | cat | ctc | act | aac | aag | ttt | gag | gac | aag | act | gtg | gca | tat | aca | 733 |
| Pro | Ser | His | Leu | Thr | Asn | Lys | Phe | Glu | Asp | Lys | Thr | Val | Ala | Tyr | Thr | |
| | | 210 | | | | | 215 | | | | | 220 | | | | |

| gag | caa | aaa | atg | acc | agt | ggc | aaa | att | aaa | aag | ttt | atc | cag | gaa | aac | 781 |
| Glu | Gln | Lys | Met | Thr | Ser | Gly | Lys | Ile | Lys | Lys | Phe | Ile | Gln | Glu | Asn | |
| 225 | | | | | 230 | | | | | 235 | | | | | | |

| att | ttt | ggt | atc | tgc | cct | cac | atg | aca | gaa | gac | aat | aaa | gat | ttg | ata | 829 |
| Ile | Phe | Gly | Ile | Cys | Pro | His | Met | Thr | Glu | Asp | Asn | Lys | Asp | Leu | Ile | |
| 240 | | | | | 245 | | | | | 250 | | | | | 255 | |

| cag | ggc | aag | gac | tta | ctt | att | gct | tac | tat | gat | gtg | gac | tat | gaa | aag | 877 |
| Gln | Gly | Lys | Asp | Leu | Leu | Ile | Ala | Tyr | Tyr | Asp | Val | Asp | Tyr | Glu | Lys | |
| | | | 260 | | | | | 265 | | | | | 270 | | | |

| aac | gct | aaa | ggt | tcc | aac | tac | tgg | aga | aac | agg | gta | atg | atg | gtg | gca | 925 |
| Asn | Ala | Lys | Gly | Ser | Asn | Tyr | Trp | Arg | Asn | Arg | Val | Met | Met | Val | Ala | |
| | | | 275 | | | | | 280 | | | | | 285 | | | |

| aag | aaa | ttc | ctg | gat | gct | ggg | cac | aaa | ctc | aac | ttt | gct | gta | gct | agc | 973 |
| Lys | Lys | Phe | Leu | Asp | Ala | Gly | His | Lys | Leu | Asn | Phe | Ala | Val | Ala | Ser | |
| | | 290 | | | | | 295 | | | | | 300 | | | | |

| cgc | aaa | acc | ttt | agc | cat | gaa | ctt | tct | gat | ttt | ggc | ttg | gag | agc | act | 1021 |
| Arg | Lys | Thr | Phe | Ser | His | Glu | Leu | Ser | Asp | Phe | Gly | Leu | Glu | Ser | Thr | |
| | | 305 | | | | | 310 | | | | | 315 | | | | |

| gct | gga | gag | att | cct | gtt | gtt | gct | atc | aga | act | gct | aaa | gga | gag | aag | 1069 |
| Ala | Gly | Glu | Ile | Pro | Val | Val | Ala | Ile | Arg | Thr | Ala | Lys | Gly | Glu | Lys | |
| 320 | | | | | 325 | | | | | 330 | | | | | 335 | |

| | | |
|---|---|---|
| ttt gtc atg cag gag gag ttc tcg cgt gat ggg aag gct ctg gag agg<br>Phe Val Met Gln Glu Glu Phe Ser Arg Asp Gly Lys Ala Leu Glu Arg<br>340 345 350 | | 1117 |
| ttc ctg cag gat tac ttt gat ggc aat ctg aag aga tac ctg aag tct<br>Phe Leu Gln Asp Tyr Phe Asp Gly Asn Leu Lys Arg Tyr Leu Lys Ser<br>355 360 365 | | 1165 |
| gaa cct atc cca gag agc aat gat ggg cct gtg aag gta gtg gta gca<br>Glu Pro Ile Pro Glu Ser Asn Asp Gly Pro Val Lys Val Val Val Ala<br>370 375 380 | | 1213 |
| gag aat ttt gat gaa ata gtg aat aat gaa aat aaa gat gtg ctg att<br>Glu Asn Phe Asp Glu Ile Val Asn Asn Glu Asn Lys Asp Val Leu Ile<br>385 390 395 | | 1261 |
| gaa ttt tat gcc cct tgg tgt ggt cat tgt aag aac ctg gag ccc aag<br>Glu Phe Tyr Ala Pro Trp Cys Gly His Cys Lys Asn Leu Glu Pro Lys<br>400 405 410 415 | | 1309 |
| tat aaa gaa ctt ggc gag aag ctc agc aaa gac cca aat atc gtc ata<br>Tyr Lys Glu Leu Gly Glu Lys Leu Ser Lys Asp Pro Asn Ile Val Ile<br>420 425 430 | | 1357 |
| gcc aag atg gat gcc aca gcc aat gat gtg cct tct cca tat gaa gtc<br>Ala Lys Met Asp Ala Thr Ala Asn Asp Val Pro Ser Pro Tyr Glu Val<br>435 440 445 | | 1405 |
| aga ggt ttt cct acc ata tac ttc tct cca gcc aac aag aag cta aat<br>Arg Gly Phe Pro Thr Ile Tyr Phe Ser Pro Ala Asn Lys Lys Leu Asn<br>450 455 460 | | 1453 |
| cca aag aaa tat gaa ggt ggc cgt gaa tta agt gat ttt att agc tat<br>Pro Lys Lys Tyr Glu Gly Gly Arg Glu Leu Ser Asp Phe Ile Ser Tyr<br>465 470 475 | | 1501 |
| cta caa aga gaa gct aca aac ccc cct gta att caa gaa gaa aaa ccc<br>Leu Gln Arg Glu Ala Thr Asn Pro Pro Val Ile Gln Glu Glu Lys Pro<br>480 485 490 495 | | 1549 |
| aag aag aag aag aag gca cag gag gat ctc taa agcagtagcc aaacaccact<br>Lys Lys Lys Lys Lys Ala Gln Glu Asp Leu<br>500 505 | | 1602 |
| ttgtaaaagg actcttccat cagagatggg aaaaccattg gggaggacta ggacccatat | | 1662 |
| gggaattatt acctctcagg gccgagagtc taga | | 1696 |

<210> SEQ ID NO 12
<211> LENGTH: 505
<212> TYPE: PRT
<213> ORGANISM: Homo sapiens

<400> SEQUENCE: 12

Met Arg Leu Arg Arg Leu Ala Leu Phe Pro Gly Val Ala Leu Leu Leu
1               5                   10                  15

Ala Ala Ala Arg Leu Ala Ala Ala Ser Asp Val Leu Glu Leu Thr Asp
                20                  25                  30

Asp Asn Phe Glu Ser Arg Ile Ser Asp Thr Gly Ser Ala Gly Leu Met
            35                  40                  45

Leu Val Glu Phe Phe Ala Pro Trp Cys Gly His Cys Lys Arg Leu Ala
        50                  55                  60

Pro Glu Tyr Glu Ala Ala Ala Thr Arg Leu Lys Gly Ile Val Pro Leu
65                  70                  75                  80

Ala Lys Val Asp Cys Thr Ala Asn Thr Asn Thr Cys Asn Lys Tyr Gly
                85                  90                  95

Val Ser Gly Tyr Pro Thr Leu Lys Ile Phe Arg Asp Gly Glu Glu Ala
                100                 105                 110

Gly Ala Tyr Asp Gly Pro Arg Thr Ala Asp Gly Ile Val Ser His Leu
            115                 120                 125

Lys Lys Gln Ala Gly Pro Ala Ser Val Pro Leu Arg Thr Glu Glu Glu
    130                 135                 140

Phe Lys Lys Phe Ile Ser Asp Lys Asp Ala Ser Ile Val Gly Phe Phe
145                 150                 155                 160

Asp Asp Ser Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Glu Tyr Asp Asp Asn Gly Glu Gly Ile Ile Leu Phe Arg Pro
        195                 200                 205

Ser His Leu Thr Asn Lys Phe Glu Asp Lys Thr Val Ala Tyr Thr Glu
    210                 215                 220

Gln Lys Met Thr Ser Gly Lys Ile Lys Lys Phe Ile Gln Glu Asn Ile
225                 230                 235                 240

Phe Gly Ile Cys Pro His Met Thr Glu Asp Asn Lys Asp Leu Ile Gln
                245                 250                 255

Gly Lys Asp Leu Leu Ile Ala Tyr Tyr Asp Val Asp Tyr Glu Lys Asn
            260                 265                 270

Ala Lys Gly Ser Asn Tyr Trp Arg Asn Arg Val Met Met Val Ala Lys
        275                 280                 285

Lys Phe Leu Asp Ala Gly His Lys Leu Asn Phe Ala Val Ala Ser Arg
290                 295                 300

Lys Thr Phe Ser His Glu Leu Ser Asp Phe Gly Leu Glu Ser Thr Ala
305                 310                 315                 320

Gly Glu Ile Pro Val Val Ala Ile Arg Thr Ala Lys Gly Glu Lys Phe
                325                 330                 335

Val Met Gln Glu Glu Phe Ser Arg Asp Gly Lys Ala Leu Glu Arg Phe
            340                 345                 350

Leu Gln Asp Tyr Phe Asp Gly Asn Leu Lys Arg Tyr Leu Lys Ser Glu
        355                 360                 365

Pro Ile Pro Glu Ser Asn Asp Gly Pro Val Lys Val Val Val Ala Glu
    370                 375                 380

Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
                405                 410                 415

Lys Glu Leu Gly Glu Lys Leu Ser Lys Asp Pro Asn Ile Val Ile Ala
            420                 425                 430

Lys Met Asp Ala Thr Ala Asn Asp Val Pro Ser Pro Tyr Glu Val Arg
        435                 440                 445

Gly Phe Pro Thr Ile Tyr Phe Ser Pro Ala Asn Lys Lys Leu Asn Pro
    450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Glu Lys Pro Lys
                485                 490                 495

Lys Lys Lys Lys Ala Gln Glu Asp Leu
            500                 505

<210> SEQ ID NO 13
<211> LENGTH: 1926
<212> TYPE: DNA
<213> ORGANISM: Homo sapiens
<220> FEATURE:
<221> NAME/KEY: CDS

<222> LOCATION: (1)..(1926)

<400> SEQUENCE: 13

```
atg gcc aaa gcc gcg gcg atc ggc atc gac ctg ggc acc acc tac tcc    48
Met Ala Lys Ala Ala Ala Ile Gly Ile Asp Leu Gly Thr Thr Tyr Ser
1               5                  10                  15 tgc gtg ggg gtg ttc caa cac ggc aag gtg gag atc atc gcc aac gac    96
Cys Val Gly Val Phe Gln His Gly Lys Val Glu Ile Ile Ala Asn Asp
            20                  25                  30 cag ggc aac cgc acc acc ccc agc tac gtg gcc ttc acg gac acc gag   144
Gln Gly Asn Arg Thr Thr Pro Ser Tyr Val Ala Phe Thr Asp Thr Glu
        35                  40                  45 cgg ctc atc ggg gat gcg gcc aag aac cag gtg gcg ctg aac ccg cag   192
Arg Leu Ile Gly Asp Ala Ala Lys Asn Gln Val Ala Leu Asn Pro Gln
    50                  55                  60 aac acc gtg ttt gac gcg aag cgg ctg atc ggc cgc aag ttc ggc gac   240
Asn Thr Val Phe Asp Ala Lys Arg Leu Ile Gly Arg Lys Phe Gly Asp
65                  70                  75                  80 ccg gtg gtg cag tcg gac atg aag cac tgg cct ttc cag gtg atc aac   288
Pro Val Val Gln Ser Asp Met Lys His Trp Pro Phe Gln Val Ile Asn
                85                  90                  95 gac gga gac aag ccc aag gtg cag gtg agc tac aag ggg gag acc aag   336
Asp Gly Asp Lys Pro Lys Val Gln Val Ser Tyr Lys Gly Glu Thr Lys
            100                 105                 110 gca ttc tac ccc gag gag atc tcg tcc atg gtg ctg acc aag atg aag   384
Ala Phe Tyr Pro Glu Glu Ile Ser Ser Met Val Leu Thr Lys Met Lys
        115                 120                 125 gag atc gcc gag gcg tac ctg ggc tac ccg gtg acc aac gcg gtg atc   432
Glu Ile Ala Glu Ala Tyr Leu Gly Tyr Pro Val Thr Asn Ala Val Ile
    130                 135                 140 acc gtg ccg gcc tac ttc aac gac tcg cag cgc cag gcc acc aag gat   480
Thr Val Pro Ala Tyr Phe Asn Asp Ser Gln Arg Gln Ala Thr Lys Asp
145                 150                 155                 160 gcg ggt gtg atc gcg ggg ctc aac gtg ctg cgg atc atc aac gag ccc   528
Ala Gly Val Ile Ala Gly Leu Asn Val Leu Arg Ile Ile Asn Glu Pro
                165                 170                 175 acg gcc gcc gcc atc gcc tac ggc ctg gac aga acg ggc aag ggg gag   576
Thr Ala Ala Ala Ile Ala Tyr Gly Leu Asp Arg Thr Gly Lys Gly Glu
            180                 185                 190 cgc aac gtg ctc atc ttt gac ctg ggc ggg ggc acc ttc gac gtg tcc   624
Arg Asn Val Leu Ile Phe Asp Leu Gly Gly Gly Thr Phe Asp Val Ser
        195                 200                 205 atc ctg acg atc gac gac ggc atc ttc gag gtg aag gcc acg gcc ggg   672
Ile Leu Thr Ile Asp Asp Gly Ile Phe Glu Val Lys Ala Thr Ala Gly
    210                 215                 220 gac acc cac ctg ggt ggg gag gac ttt gac aac agg ctg gtg aac cac   720
Asp Thr His Leu Gly Gly Glu Asp Phe Asp Asn Arg Leu Val Asn His
225                 230                 235                 240 ttc gtg gag gag ttc aag aga aaa cac aag aag gac atc agc cag aac   768
Phe Val Glu Glu Phe Lys Arg Lys His Lys Lys Asp Ile Ser Gln Asn
                245                 250                 255 aag cga gcc gtg agg cgg ctg cgc acc gcc tgc gag agg gcc aag agg   816
Lys Arg Ala Val Arg Arg Leu Arg Thr Ala Cys Glu Arg Ala Lys Arg
            260                 265                 270 acc ctg tcg tcc agc acc cag gcc agc ctg gag atc gac tcc ctg ttt   864
Thr Leu Ser Ser Ser Thr Gln Ala Ser Leu Glu Ile Asp Ser Leu Phe
        275                 280                 285 gag ggc atc gac ttc tac acg tcc atc acc agg gcg agg ttc gag gag   912
Glu Gly Ile Asp Phe Tyr Thr Ser Ile Thr Arg Ala Arg Phe Glu Glu
    290                 295                 300
```

-continued

| | | |
|---|---|---|
| ctg tgc tcc gac ctg ttc cga agc acc ctg gag ccc gtg gag aag gct<br>Leu Cys Ser Asp Leu Phe Arg Ser Thr Leu Glu Pro Val Glu Lys Ala<br>305                    310                    315                    320 | 960 |
| ctg cgc gac gcc aag ctg gac aag gcc cag att cac gac ctg gtc ctg<br>Leu Arg Asp Ala Lys Leu Asp Lys Ala Gln Ile His Asp Leu Val Leu<br>                    325                    330                    335 | 1008 |
| gtc ggg ggc tcc acc cgc atc ccc aag gtg cag aag ctg ctg cag gac<br>Val Gly Gly Ser Thr Arg Ile Pro Lys Val Gln Lys Leu Leu Gln Asp<br>              340                    345                    350 | 1056 |
| ttc ttc aac ggg cgc gac ctg aac aag agc atc aac ccc gac gag gct<br>Phe Phe Asn Gly Arg Asp Leu Asn Lys Ser Ile Asn Pro Asp Glu Ala<br>355                    360                    365 | 1104 |
| gtg gcc tac ggg gcg gcg gtg cag gcg gcc atc ctg atg ggg gac aag<br>Val Ala Tyr Gly Ala Ala Val Gln Ala Ala Ile Leu Met Gly Asp Lys<br>             370                    375                    380 | 1152 |
| tcc gag aac gtg cag gac ctg ctg ctg ctg gac gtg gct ccc ctg tcg<br>Ser Glu Asn Val Gln Asp Leu Leu Leu Leu Asp Val Ala Pro Leu Ser<br>385                    390                    395                    400 | 1200 |
| ctg ggg ctg gag acg gcc gga ggc gtg atg act gcc ctg atc aag cgc<br>Leu Gly Leu Glu Thr Ala Gly Gly Val Met Thr Ala Leu Ile Lys Arg<br>                    405                    410                    415 | 1248 |
| aac tcc acc atc ccc acc aag cag acg cag atc ttc acc acc tac tcc<br>Asn Ser Thr Ile Pro Thr Lys Gln Thr Gln Ile Phe Thr Thr Tyr Ser<br>             420                    425                    430 | 1296 |
| gac aac caa ccc ggg gtg ctg atc cag gtg tac gag ggc gag agg gcc<br>Asp Asn Gln Pro Gly Val Leu Ile Gln Val Tyr Glu Gly Glu Arg Ala<br>435                    440                    445 | 1344 |
| atg acg aaa gac aac aat ctg ttg ggg cgc ttc gag ctg agc ggc atc<br>Met Thr Lys Asp Asn Asn Leu Leu Gly Arg Phe Glu Leu Ser Gly Ile<br>             450                    455                    460 | 1392 |
| cct ccg gcc ccc agg ggc gtg ccc cag atc gag gtg acc ttc gac atc<br>Pro Pro Ala Pro Arg Gly Val Pro Gln Ile Glu Val Thr Phe Asp Ile<br>465                    470                    475                    480 | 1440 |
| gat gcc aac ggc atc ctg aac gtc acg gcc acg gac aag agc acc ggc<br>Asp Ala Asn Gly Ile Leu Asn Val Thr Ala Thr Asp Lys Ser Thr Gly<br>                    485                    490                    495 | 1488 |
| aag gcc aac aag atc acc atc acc aac gac aag ggc cgc ctg agc aag<br>Lys Ala Asn Lys Ile Thr Ile Thr Asn Asp Lys Gly Arg Leu Ser Lys<br>             500                    505                    510 | 1536 |
| gag gag atc gag cgc atg gtg cag gag gcg gag aag tac aaa gcg gag<br>Glu Glu Ile Glu Arg Met Val Gln Glu Ala Glu Lys Tyr Lys Ala Glu<br>515                    520                    525 | 1584 |
| gac gag gtg cag cgc gag agg gtg tca gcc aag aac gcc ctg gag tcc<br>Asp Glu Val Gln Arg Glu Arg Val Ser Ala Lys Asn Ala Leu Glu Ser<br>             530                    535                    540 | 1632 |
| tac gcc ttc aac atg aag agc gcc gtg gag gat gag ggg ctc aag ggc<br>Tyr Ala Phe Asn Met Lys Ser Ala Val Glu Asp Glu Gly Leu Lys Gly<br>545                    550                    555                    560 | 1680 |
| aag atc agc gag gcc gac aag aag aag gtg ctg gac aag tgt caa gag<br>Lys Ile Ser Glu Ala Asp Lys Lys Lys Val Leu Asp Lys Cys Gln Glu<br>                    565                    570                    575 | 1728 |
| gtc atc tcg tgg ctg gac gcc aac acc ttg gcc gag aag gac gag ttt<br>Val Ile Ser Trp Leu Asp Ala Asn Thr Leu Ala Glu Lys Asp Glu Phe<br>             580                    585                    590 | 1776 |
| gag cac aag agg aag gag ctg gag cag gtg tgt aac ccc atc atc agc<br>Glu His Lys Arg Lys Glu Leu Glu Gln Val Cys Asn Pro Ile Ile Ser<br>             595                    600                    605 | 1824 |
| gga ctg tac cag ggt gcc ggt ggt ccc ggg cct ggg ggc ttc ggg gct<br>Gly Leu Tyr Gln Gly Ala Gly Gly Pro Gly Pro Gly Gly Phe Gly Ala<br>             610                    615                    620 | 1872 |

```
cag ggt ccc aag gga ggg tct ggg tca ggc ccc acc att gag gag gta     1920
Gln Gly Pro Lys Gly Gly Ser Gly Ser Gly Pro Thr Ile Glu Glu Val
625                 630                 635                 640 gat tag                                                              1926
Asp

<210> SEQ ID NO 14
<211> LENGTH: 641
<212> TYPE: PRT
<213> ORGANISM: Homo sapiens

<400> SEQUENCE: 14

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Ile
        130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350
```

```
Phe Phe Asn Gly Arg Asp Leu Asn Lys Ser Ile Asn Pro Asp Glu Ala
            355                 360                 365
Val Ala Tyr Gly Ala Ala Val Gln Ala Ala Ile Leu Met Gly Asp Lys
        370                 375                 380
Ser Glu Asn Val Gln Asp Leu Leu Leu Leu Asp Val Ala Pro Leu Ser
385                 390                 395                 400
Leu Gly Leu Glu Thr Ala Gly Gly Val Met Thr Ala Leu Ile Lys Arg
                405                 410                 415
Asn Ser Thr Ile Pro Thr Lys Gln Thr Gln Ile Phe Thr Thr Tyr Ser
            420                 425                 430
Asp Asn Gln Pro Gly Val Leu Ile Gln Val Tyr Glu Gly Glu Arg Ala
        435                 440                 445
Met Thr Lys Asp Asn Asn Leu Leu Gly Arg Phe Glu Leu Ser Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                485                 490                 495
Lys Ala Asn Lys Ile Thr Ile Thr Asn Asp Lys Gly Arg Leu Ser Lys
            500                 505                 510
Glu Glu Ile Glu Arg Met Val Gln Glu Ala Lys Tyr Lys Ala Glu
        515                 520                 525
Asp Glu Val Gln Arg Glu Arg Val Ser Ala Lys Asn Ala Leu Glu Ser
    530                 535                 540
Tyr Ala Phe Asn Met Lys Ser Ala Val Glu Asp Glu Gly Leu Lys Gly
545                 550                 555                 560
Lys Ile Ser Glu Ala Asp Lys Lys Lys Val Leu Asp Lys Cys Gln Glu
                565                 570                 575
Val Ile Ser Trp Leu Asp Ala Asn Thr Leu Ala Glu Lys Asp Glu Phe
            580                 585                 590
Glu His Lys Arg Lys Glu Leu Glu Gln Val Cys Asn Pro Ile Ile Ser
        595                 600                 605
Gly Leu Tyr Gln Gly Ala Gly Gly Pro Gly Pro Gly Gly Phe Gly Ala
    610                 615                 620
Gln Gly Pro Lys Gly Gly Ser Gly Ser Gly Pro Thr Ile Glu Glu Val
625                 630                 635                 640
Asp
```

<210> SEQ ID NO 15
<211> LENGTH: 1023
<212> TYPE: DNA
<213> ORGANISM: Homo sapiens
<220> FEATURE:
<221> NAME/KEY: CDS
<222> LOCATION: (1)..(1023)

<400> SEQUENCE: 15

```
atg ggt aaa gac tac tac cag acg ttg ggc ctg gcc cgc ggc gcg tcg      48
Met Gly Lys Asp Tyr Tyr Gln Thr Leu Gly Leu Ala Arg Gly Ala Ser
1               5                   10                  15 gac gag gag atc aag cgg gcc tac cgc cgc cag gcg ctg cgc tac cac      96
Asp Glu Glu Ile Lys Arg Ala Tyr Arg Arg Gln Ala Leu Arg Tyr His
                20                  25                  30 ccg gac aag aac aag gag ccc ggc gcc gag gag aag ttc aag gag atc     144
Pro Asp Lys Asn Lys Glu Pro Gly Ala Glu Glu Lys Phe Lys Glu Ile
            35                  40                  45
```

| | | | | | | | | | | | | | | | | |
|---|---|---|---|---|---|---|---|---|---|---|---|---|---|---|---|---|
| gct | gag | gcc | tac | gac | gtg | ctc | agc | gac | ccg | cgc | aag | cgc | gag | atc | ttc | 192 |
| Ala | Glu | Ala | Tyr | Asp | Val | Leu | Ser | Asp | Pro | Arg | Lys | Arg | Glu | Ile | Phe | |
| | 50 | | | | 55 | | | | | 60 | | | | | | |
| gac | cgc | tac | ggg | gag | gaa | ggc | cta | aag | ggg | agt | ggc | ccc | agt | ggc | ggt | 240 |
| Asp | Arg | Tyr | Gly | Glu | Glu | Gly | Leu | Lys | Gly | Ser | Gly | Pro | Ser | Gly | Gly | |
| 65 | | | | | 70 | | | | | 75 | | | | | 80 | |
| agc | ggc | ggt | ggt | gcc | aat | ggt | acc | tct | ttc | agc | tac | aca | ttc | cat | gga | 288 |
| Ser | Gly | Gly | Gly | Ala | Asn | Gly | Thr | Ser | Phe | Ser | Tyr | Thr | Phe | His | Gly | |
| | | | | | 85 | | | | | 90 | | | | | 95 | |
| gac | cct | cat | gcc | atg | ttt | gct | gag | ttc | ttc | ggt | ggc | aga | aat | ccc | ttt | 336 |
| Asp | Pro | His | Ala | Met | Phe | Ala | Glu | Phe | Phe | Gly | Gly | Arg | Asn | Pro | Phe | |
| | | | | 100 | | | | | 105 | | | | | 110 | | |
| gac | acc | ttt | ttt | ggg | cag | cgg | aac | ggg | gag | gaa | ggc | atg | gac | att | gat | 384 |
| Asp | Thr | Phe | Phe | Gly | Gln | Arg | Asn | Gly | Glu | Glu | Gly | Met | Asp | Ile | Asp | |
| | | 115 | | | | | 120 | | | | | 125 | | | | |
| gac | cca | ttc | tct | ggc | ttc | cct | atg | ggc | atg | ggt | ggc | ttc | acc | aac | gtg | 432 |
| Asp | Pro | Phe | Ser | Gly | Phe | Pro | Met | Gly | Met | Gly | Gly | Phe | Thr | Asn | Val | |
| 130 | | | | | 135 | | | | | 140 | | | | | | |
| aac | ttt | ggc | cgc | tcc | cgc | tct | gcc | caa | gag | ccc | gcc | cga | aag | aag | caa | 480 |
| Asn | Phe | Gly | Arg | Ser | Arg | Ser | Ala | Gln | Glu | Pro | Ala | Arg | Lys | Lys | Gln | |
| 145 | | | | | 150 | | | | | 155 | | | | | 160 | |
| gat | ccc | cca | gtc | acc | cac | gac | ctt | cga | gtc | tcc | ctt | gaa | gag | atc | tac | 528 |
| Asp | Pro | Pro | Val | Thr | His | Asp | Leu | Arg | Val | Ser | Leu | Glu | Glu | Ile | Tyr | |
| | | | | | 165 | | | | | 170 | | | | | 175 | |
| agc | ggc | tgt | acc | aag | aag | atg | aaa | atc | tcc | cac | aag | cgg | cta | aac | ccc | 576 |
| Ser | Gly | Cys | Thr | Lys | Lys | Met | Lys | Ile | Ser | His | Lys | Arg | Leu | Asn | Pro | |
| | | | 180 | | | | | 185 | | | | | 190 | | | |
| gac | gga | aag | agc | att | cga | aac | gaa | gac | aaa | ata | ttg | acc | atc | gaa | gtg | 624 |
| Asp | Gly | Lys | Ser | Ile | Arg | Asn | Glu | Asp | Lys | Ile | Leu | Thr | Ile | Glu | Val | |
| | | 195 | | | | | 200 | | | | | 205 | | | | |
| aag | aag | ggg | tgg | aaa | gaa | gga | acc | aaa | atc | act | ttc | ccc | aag | gaa | gga | 672 |
| Lys | Lys | Gly | Trp | Lys | Glu | Gly | Thr | Lys | Ile | Thr | Phe | Pro | Lys | Glu | Gly | |
| 210 | | | | | 215 | | | | | 220 | | | | | | |
| gac | cag | acc | tcc | aac | aac | att | cca | gct | gat | atc | gtc | ttt | gtt | tta | aag | 720 |
| Asp | Gln | Thr | Ser | Asn | Asn | Ile | Pro | Ala | Asp | Ile | Val | Phe | Val | Leu | Lys | |
| 225 | | | | | 230 | | | | | 235 | | | | | 240 | |
| gac | aag | ccc | cac | aat | atc | ttt | aag | aga | gat | ggc | tct | gat | gtc | att | tat | 768 |
| Asp | Lys | Pro | His | Asn | Ile | Phe | Lys | Arg | Asp | Gly | Ser | Asp | Val | Ile | Tyr | |
| | | | | 245 | | | | | 250 | | | | | 255 | | |
| cct | gcc | agg | atc | agc | ctc | cgg | gag | gct | ctg | tgt | ggc | tgc | aca | gtg | aac | 816 |
| Pro | Ala | Arg | Ile | Ser | Leu | Arg | Glu | Ala | Leu | Cys | Gly | Cys | Thr | Val | Asn | |
| | | | 260 | | | | | 265 | | | | | 270 | | | |
| gtc | ccc | act | ctg | gac | ggc | agg | acg | ata | ccc | gtc | gta | ttc | aaa | gat | gtt | 864 |
| Val | Pro | Thr | Leu | Asp | Gly | Arg | Thr | Ile | Pro | Val | Val | Phe | Lys | Asp | Val | |
| | | 275 | | | | | 280 | | | | | 285 | | | | |
| atc | agg | cct | ggc | atg | cgg | cga | aaa | gtt | cct | gga | gaa | ggc | ctc | ccc | ctc | 912 |
| Ile | Arg | Pro | Gly | Met | Arg | Arg | Lys | Val | Pro | Gly | Glu | Gly | Leu | Pro | Leu | |
| 290 | | | | | 295 | | | | | 300 | | | | | | |
| ccc | aaa | aca | ccc | gag | aaa | cgt | ggg | gac | ctc | att | att | gag | ttt | gaa | gtg | 960 |
| Pro | Lys | Thr | Pro | Glu | Lys | Arg | Gly | Asp | Leu | Ile | Ile | Glu | Phe | Glu | Val | |
| 305 | | | | | 310 | | | | | 315 | | | | | 320 | |
| atc | ttc | ccc | gaa | agg | att | ccc | cag | aca | tca | aga | acc | gta | ctt | gag | cag | 1008 |
| Ile | Phe | Pro | Glu | Arg | Ile | Pro | Gln | Thr | Ser | Arg | Thr | Val | Leu | Glu | Gln | |
| | | | | 325 | | | | | 330 | | | | | 335 | | |
| gtt | ctt | cca | ata | tag | | | | | | | | | | | | 1023 |
| Val | Leu | Pro | Ile | | | | | | | | | | | | | |
| | | | 340 | | | | | | | | | | | | | |

<210> SEQ ID NO 16
<211> LENGTH: 340
<212> TYPE: PRT

<213> ORGANISM: Homo sapiens

<400> SEQUENCE: 16

```
Met Gly Lys Asp Tyr Tyr Gln Thr Leu Gly Leu Ala Arg Gly Ala Ser
1               5                   10                  15

Asp Glu Glu Ile Lys Arg Ala Tyr Arg Arg Gln Ala Leu Arg Tyr His
            20                  25                  30

Pro Asp Lys Asn Lys Glu Pro Gly Ala Glu Lys Phe Lys Glu Ile
        35                  40                  45

Ala Glu Ala Tyr Asp Val Leu Ser Asp Pro Arg Lys Arg Glu Ile Phe
    50                  55                  60

Asp Arg Tyr Gly Glu Glu Gly Leu Lys Gly Ser Gly Pro Ser Gly Gly
65                  70                  75                  80

Ser Gly Gly Gly Ala Asn Gly Thr Ser Phe Ser Tyr Thr Phe His Gly
                85                  90                  95

Asp Pro His Ala Met Phe Ala Glu Phe Phe Gly Gly Arg Asn Pro Phe
            100                 105                 110

Asp Thr Phe Phe Gly Gln Arg Asn Gly Glu Glu Gly Met Asp Ile Asp
        115                 120                 125

Asp Pro Phe Ser Gly Phe Pro Met Gly Met Gly Gly Phe Thr Asn Val
    130                 135                 140

Asn Phe Gly Arg Ser Arg Ser Ala Gln Glu Pro Ala Arg Lys Lys Gln
145                 150                 155                 160

Asp Pro Pro Val Thr His Asp Leu Arg Val Ser Leu Glu Glu Ile Tyr
                165                 170                 175

Ser Gly Cys Thr Lys Lys Met Lys Ile Ser His Lys Arg Leu Asn Pro
            180                 185                 190

Asp Gly Lys Ser Ile Arg Asn Glu Asp Lys Ile Leu Thr Ile Glu Val
        195                 200                 205

Lys Lys Gly Trp Lys Glu Gly Thr Lys Ile Thr Phe Pro Lys Glu Gly
    210                 215                 220

Asp Gln Thr Ser Asn Asn Ile Pro Ala Asp Ile Val Phe Val Leu Lys
225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
            260                 265                 270

Val Pro Thr Leu Asp Gly Arg Thr Ile Pro Val Val Phe Lys Asp Val
        275                 280                 285

Ile Arg Pro Gly Met Arg Arg Lys Val Pro Gly Glu Gly Leu Pro Leu
    290                 295                 300

Pro Lys Thr Pro Glu Lys Arg Gly Asp Leu Ile Ile Glu Phe Glu Val
305                 310                 315                 320

Ile Phe Pro Glu Arg Ile Pro Gln Thr Ser Arg Thr Val Leu Glu Gln
                325                 330                 335

Val Leu Pro Ile
            340
```

<210> SEQ ID NO 17
<211> LENGTH: 1122
<212> TYPE: DNA
<213> ORGANISM: Homo sapiens
<220> FEATURE:
<221> NAME/KEY: CDS
<222> LOCATION: (1)..(1122)

<400> SEQUENCE: 17

-continued

| | |
|---|---:|
| atg acc acc tca gca agt tcc cac tta aat aaa ggc atc aag cag gtg<br>Met Thr Thr Ser Ala Ser Ser His Leu Asn Lys Gly Ile Lys Gln Val<br>1               5                   10                  15 | 48 |
| tac atg tcc ctg cct cag ggt gag aaa gtc cag gcc atg tat atc tgg<br>Tyr Met Ser Leu Pro Gln Gly Glu Lys Val Gln Ala Met Tyr Ile Trp<br>            20                  25                  30 | 96 |
| atc gat ggt act gga gaa gga ctg cgc tgc aag acc cgg acc ctg gac<br>Ile Asp Gly Thr Gly Glu Gly Leu Arg Cys Lys Thr Arg Thr Leu Asp<br>        35                  40                  45 | 144 |
| agt gag ccc aag tgt gtg gaa gag ttg cct gag tgg aat ttc gat ggc<br>Ser Glu Pro Lys Cys Val Glu Glu Leu Pro Glu Trp Asn Phe Asp Gly<br>    50                  55                  60 | 192 |
| tcc agt act tta cag tct gag ggt tcc aac agt gac atg tat ctc gtg<br>Ser Ser Thr Leu Gln Ser Glu Gly Ser Asn Ser Asp Met Tyr Leu Val<br>65                  70                  75                  80 | 240 |
| cct gct gcc atg ttt cgg gac ccc ttc cgt aag gac cct aac aag ctg<br>Pro Ala Ala Met Phe Arg Asp Pro Phe Arg Lys Asp Pro Asn Lys Leu<br>                85                  90                  95 | 288 |
| gtg tta tgt gaa gtt ttc aag tac aat cga agg cct gca gag acc aat<br>Val Leu Cys Glu Val Phe Lys Tyr Asn Arg Arg Pro Ala Glu Thr Asn<br>            100                 105                 110 | 336 |
| ttg agg cac acc tgt aaa cgg ata atg gac atg gtg agc aac cag cac<br>Leu Arg His Thr Cys Lys Arg Ile Met Asp Met Val Ser Asn Gln His<br>        115                 120                 125 | 384 |
| ccc tgg ttt ggc atg gag cag gag tat acc ctc atg ggg aca gat ggg<br>Pro Trp Phe Gly Met Glu Gln Glu Tyr Thr Leu Met Gly Thr Asp Gly<br>    130                 135                 140 | 432 |
| cac ccc ttt ggt tgg cct tcc aac ggc ttc cca ggg ccc cag ggt cca<br>His Pro Phe Gly Trp Pro Ser Asn Gly Phe Pro Gly Pro Gln Gly Pro<br>145                 150                 155                 160 | 480 |
| tat tac tgt ggt gtg gga gca gac aga gcc tat ggc agg gac atc gtg<br>Tyr Tyr Cys Gly Val Gly Ala Asp Arg Ala Tyr Gly Arg Asp Ile Val<br>                165                 170                 175 | 528 |
| gag gcc cat tac cgg gcc tgc ttg tat gct gga gtc aag att gcg ggg<br>Glu Ala His Tyr Arg Ala Cys Leu Tyr Ala Gly Val Lys Ile Ala Gly<br>            180                 185                 190 | 576 |
| act aat gcc gag gtc atg cct gcc cag tgg gaa ttt cag att gga cct<br>Thr Asn Ala Glu Val Met Pro Ala Gln Trp Glu Phe Gln Ile Gly Pro<br>        195                 200                 205 | 624 |
| tgt gaa gga atc agc atg gga gat cat ctc tgg gtg gcc cgt ttc atc<br>Cys Glu Gly Ile Ser Met Gly Asp His Leu Trp Val Ala Arg Phe Ile<br>    210                 215                 220 | 672 |
| ttg cat cgt gtg tgt gaa gac ttt gga gtg ata gca acc ttt gat cct<br>Leu His Arg Val Cys Glu Asp Phe Gly Val Ile Ala Thr Phe Asp Pro<br>225                 230                 235                 240 | 720 |
| aag ccc att cct ggg aac tgg aat ggt gca ggc tgc cat acc aac ttc<br>Lys Pro Ile Pro Gly Asn Trp Asn Gly Ala Gly Cys His Thr Asn Phe<br>                245                 250                 255 | 768 |
| agc acc aag gcc atg cgg gag gag aat ggt ctg aag tac atc gag gag<br>Ser Thr Lys Ala Met Arg Glu Glu Asn Gly Leu Lys Tyr Ile Glu Glu<br>            260                 265                 270 | 816 |
| gcc att gag aaa cta agc aag cgg cac cag tac cac atc cgt gcc tat<br>Ala Ile Glu Lys Leu Ser Lys Arg His Gln Tyr His Ile Arg Ala Tyr<br>        275                 280                 285 | 864 |
| gat ccc aag gga ggc ctg gac aat gcc cga cgt cta act gga ttc cat<br>Asp Pro Lys Gly Gly Leu Asp Asn Ala Arg Arg Leu Thr Gly Phe His<br>    290                 295                 300 | 912 |
| gaa acc tcc aac atc aac gac ttt tct gct ggt gta gcc aat cgt agc<br>Glu Thr Ser Asn Ile Asn Asp Phe Ser Ala Gly Val Ala Asn Arg Ser<br>305                 310                 315                 320 | 960 |

```
gcc agc ata cgc att ccc cgg act gtt ggc cag gag aag aag ggt tac    1008
Ala Ser Ile Arg Ile Pro Arg Thr Val Gly Gln Glu Lys Lys Gly Tyr
            325                 330                 335 ttt gaa gat cgt cgc ccc tct gcc aac tgc gac ccc ttt tcg gtg aca    1056
Phe Glu Asp Arg Arg Pro Ser Ala Asn Cys Asp Pro Phe Ser Val Thr
            340                 345                 350 gaa gcc ctc atc cgc acg tgt ctt ctc aat gaa acc ggc gat gag ccc    1104
Glu Ala Leu Ile Arg Thr Cys Leu Leu Asn Glu Thr Gly Asp Glu Pro
            355                 360                 365 ttc cag tac aaa aat taa                                            1122
Phe Gln Tyr Lys Asn
            370

<210> SEQ ID NO 18
<211> LENGTH: 373
<212> TYPE: PRT
<213> ORGANISM: Homo sapiens

<400> SEQUENCE: 18

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
            20                  25                  30

Ile Asp Gly Thr Gly Glu Gly Leu Arg Cys Lys Thr Arg Thr Leu Asp
            35                  40                  45

Ser Glu Pro Lys Cys Val Glu Glu Leu Pro Glu Trp Asn Phe Asp Gly
        50                  55                  60

Ser Ser Thr Leu Gln Ser Glu Gly Ser Asn Ser Asp Met Tyr Leu Val
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
            115                 120                 125

Pro Trp Phe Gly Met Glu Gln Glu Tyr Thr Leu Met Gly Thr Asp Gly
        130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
            195                 200                 205

Cys Glu Gly Ile Ser Met Gly Asp His Leu Trp Val Ala Arg Phe Ile
        210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270

Ala Ile Glu Lys Leu Ser Lys Arg His Gln Tyr His Ile Arg Ala Tyr
            275                 280                 285

Asp Pro Lys Gly Gly Leu Asp Asn Ala Arg Arg Leu Thr Gly Phe His
```

```
                    290                 295                 300
Glu Thr Ser Asn Ile Asn Asp Phe Ser Ala Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
        370

<210> SEQ ID NO 19
<211> LENGTH: 170
<212> TYPE: PRT
<213> ORGANISM: Homo sapiens

<400> SEQUENCE: 19

Ala Asp Arg Glu Arg Ser Ile His Asp Phe Cys Leu Val Ser Lys Val
1               5                   10                  15

Val Gly Arg Cys Arg Ala Ser Met Pro Arg Trp Trp Tyr Asn Val Thr
                20                  25                  30

Asp Gly Ser Cys Gln Leu Phe Val Tyr Gly Gly Cys Asp Gly Asn Ser
            35                  40                  45

Asn Asn Tyr Leu Thr Lys Glu Glu Cys Leu Lys Lys Cys Ala Thr Val
        50                  55                  60

Thr Glu Asn Ala Thr Gly Asp Leu Ala Thr Ser Arg Asn Ala Ala Asp
65                  70                  75                  80

Ser Ser Val Pro Ser Ala Pro Arg Arg Gln Asp Ser Glu Asp His Ser
                85                  90                  95

Ser Asp Met Phe Asn Tyr Glu Glu Tyr Cys Thr Ala Asn Ala Val Thr
            100                 105                 110

Gly Pro Cys Arg Ala Ser Phe Pro Arg Trp Tyr Phe Asp Val Glu Arg
        115                 120                 125

Asn Ser Cys Asn Asn Phe Ile Tyr Gly Gly Cys Arg Gly Asn Lys Asn
    130                 135                 140

Ser Tyr Arg Ser Glu Glu Ala Cys Met Leu Arg Cys Phe Arg Gln Gln
145                 150                 155                 160

Glu Asn Pro Pro Leu Pro Leu Gly Ser Lys
                165                 170

<210> SEQ ID NO 20
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 20
agggaaccgc atggccaaag                                              20

<210> SEQ ID NO 21
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 21
```

```
gaaaggcccc taatctacct cctca                                              25

<210> SEQ ID NO 22
<211> LENGTH: 3
<212> TYPE: PRT
<213> ORGANISM: Artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-benzoyl
<220> FEATURE:
<221> NAME/KEY: MISC_FEATURE
<222> LOCATION: (3)..(3)
<223> OTHER INFORMATION: Xaa is Arg-pNA

<400> SEQUENCE: 22

Pro Phe Xaa
1
```